(12) United States Patent
Jørgensen et al.

(10) Patent No.: US 7,368,254 B2
(45) Date of Patent: May 6, 2008

(54) LIPID-BASED SYSTEMS FOR TARGETING DIAGNOSTIC AGENTS

(75) Inventors: Kent Jørgensen, Bagsværd (DK); Jesper Davidsen, Copenhagen Ø (DK); Charlotte Vermehren, Holte (DK); Sven Frøkjær, Holte (DK); Ole G. Mouritsen, Klampenborg (DK)

(73) Assignee: Liplasome Pharma A/S, Lyngby (DK)

( * ) Notice: Subject to any disclaimer, the term of this patent is extended or adjusted under 35 U.S.C. 154(b) by 783 days.

(21) Appl. No.: 10/239,515

(22) PCT Filed: Apr. 11, 2001

(86) PCT No.: PCT/DK01/00269

§ 371 (c)(1),
(2), (4) Date: Feb. 11, 2003

(87) PCT Pub. No.: WO01/76644

PCT Pub. Date: Oct. 18, 2001

(65) Prior Publication Data

US 2003/0175205 A1  Sep. 18, 2003

(30) Foreign Application Priority Data

Apr. 12, 2000 (DK) ............... 2000 00616

(51) Int. Cl.
*A61K 51/00* (2006.01)
*A61K 49/00* (2006.01)
*A61M 36/00* (2006.01)

(52) U.S. Cl. ........... 435/7.23; 424/1.37; 424/1.65; 424/9.1; 424/9.3

(58) Field of Classification Search ........ 514/642, 514/144, 557; 424/1.37, 1.65, 9.1, 9.3, 9.32, 424/9.321
See application file for complete search history.

(56) References Cited

U.S. PATENT DOCUMENTS 4,837,028 A   6/1989   Allen
5,013,556 A   5/1991   Woodle et al.
5,213,804 A * 5/1993   Martin et al. ............... 424/450
5,705,187 A * 1/1998   Unger ......................... 424/450
5,770,222 A * 6/1998   Unger et al. ................ 424/450
6,120,751 A * 9/2000   Unger ......................... 424/9.51

OTHER PUBLICATIONS

Vermehren et al. (Biochim Biophys. Acta 1998; 1373: Abst.).*
Kaiser (Critical Reviews in Clinical Laboratory Sciences 1999; 36: 65-163).*
Khalifa et al. (Nucl. Med. Commun. 1997; 18: 17-23).*
Kaiser (Critical Reviews in Clinical Laboratory Sciences 1999; 36: 65-163).*
Khalifa et al. (Nucl. Med. Commun. 1997; 18: 17-23).*
Jorgensen et al. (Pharmaceutical Research 1999; 16: 1491-1493).*
Davidsen et al. (Symposium on lipid and surfactant self-assemblies: Structure, Dynamics and Reactions Feb. 24-25, 2000, Uppsala, Sweden; 1-16).*
Davidsen et al. ("Controlled destabilization of liposomal drug delivery systems by phospholipase A2" 1999).*
Hong et al. (J. Med. Chem. 1986; 29; 2038-2044).*
Apte et al. (FEBS Letters 1990; 265; 104-106).*
B. Kleuser et al., Chemistry and Physics of Lipids, vol. 79, pp. 29-37, No. 1 (1996).
Kaiser, "Phospholipase A2: Its Usefulness in Labortory Diagnostics", Critical Reviews in Clinical Laboratory Sciences, 36(2):65-163 (1999).
Torchilin, "Liposomes as carriers of contrast agents for in vivo diagnositcs", Lasic and Papahadjopoulos (eds.), Medical Applications of Liposomes, pp. 515-543, 1998.
Ogihara et al., "Differential Uptake Gallium-67-Labeled Liposomes Between Tumors and Inflammatory Lesions in Rats", J. Nucl. Med. 27: 1300-1307 (1986).

* cited by examiner

*Primary Examiner*—Brandon Fetterolf
(74) *Attorney, Agent, or Firm*—Birch, Stewart, Kolasch & Birch, LLP

(57) ABSTRACT

The invention relates to targeting of diagnostic agents by use of lipid-based compositions. The invention is useful in the diagnosis of various disorders which are associated with or resulting from increased levels of extracellular $PLA_2$ activity in the diseased tissue, e.g. cancer, infectious, and inflammatory conditions.

17 Claims, 18 Drawing Sheets

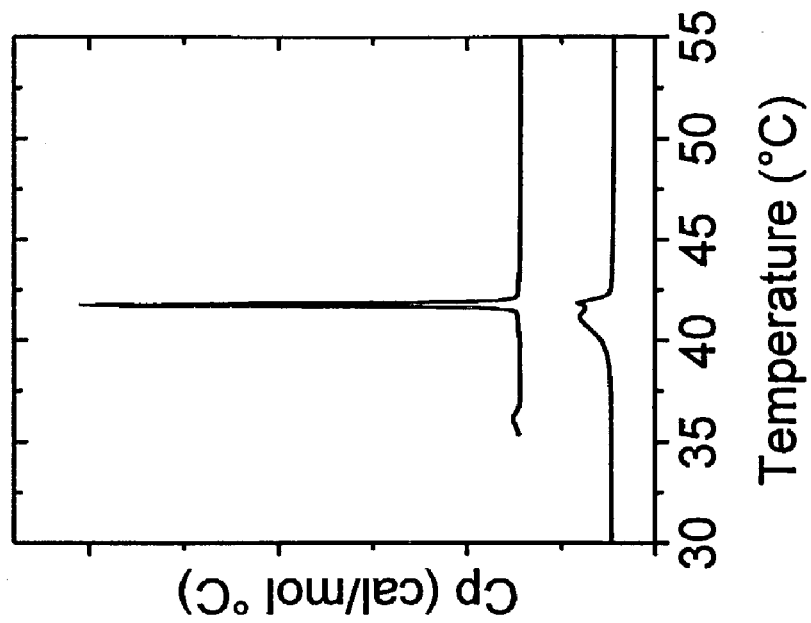
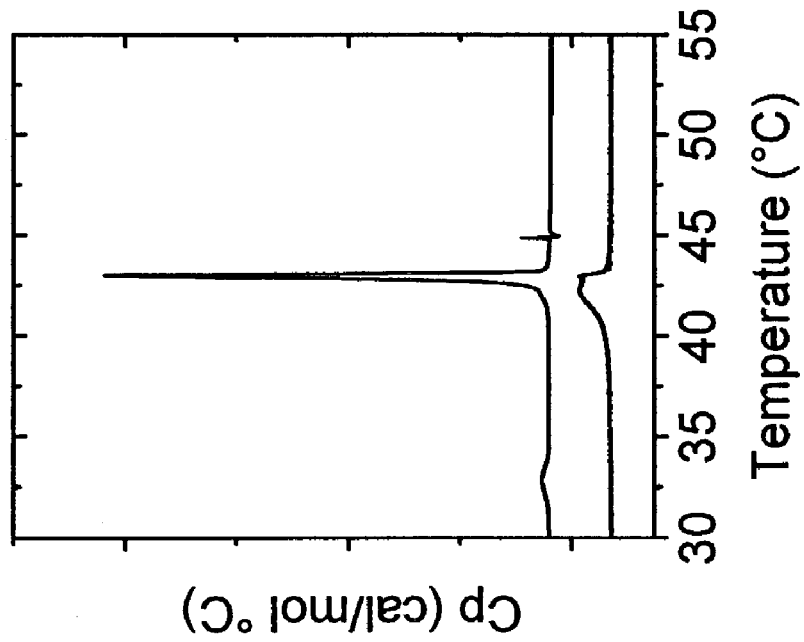
Fig. 1

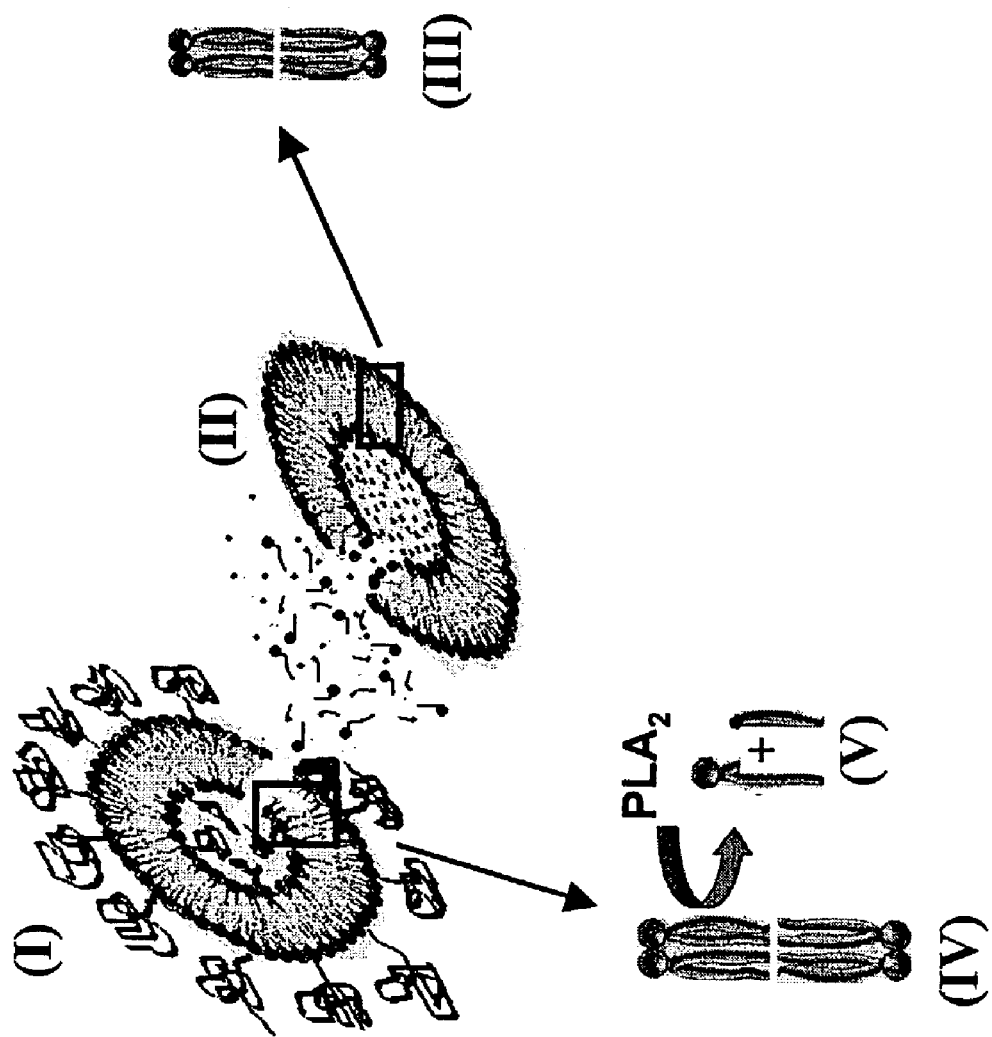

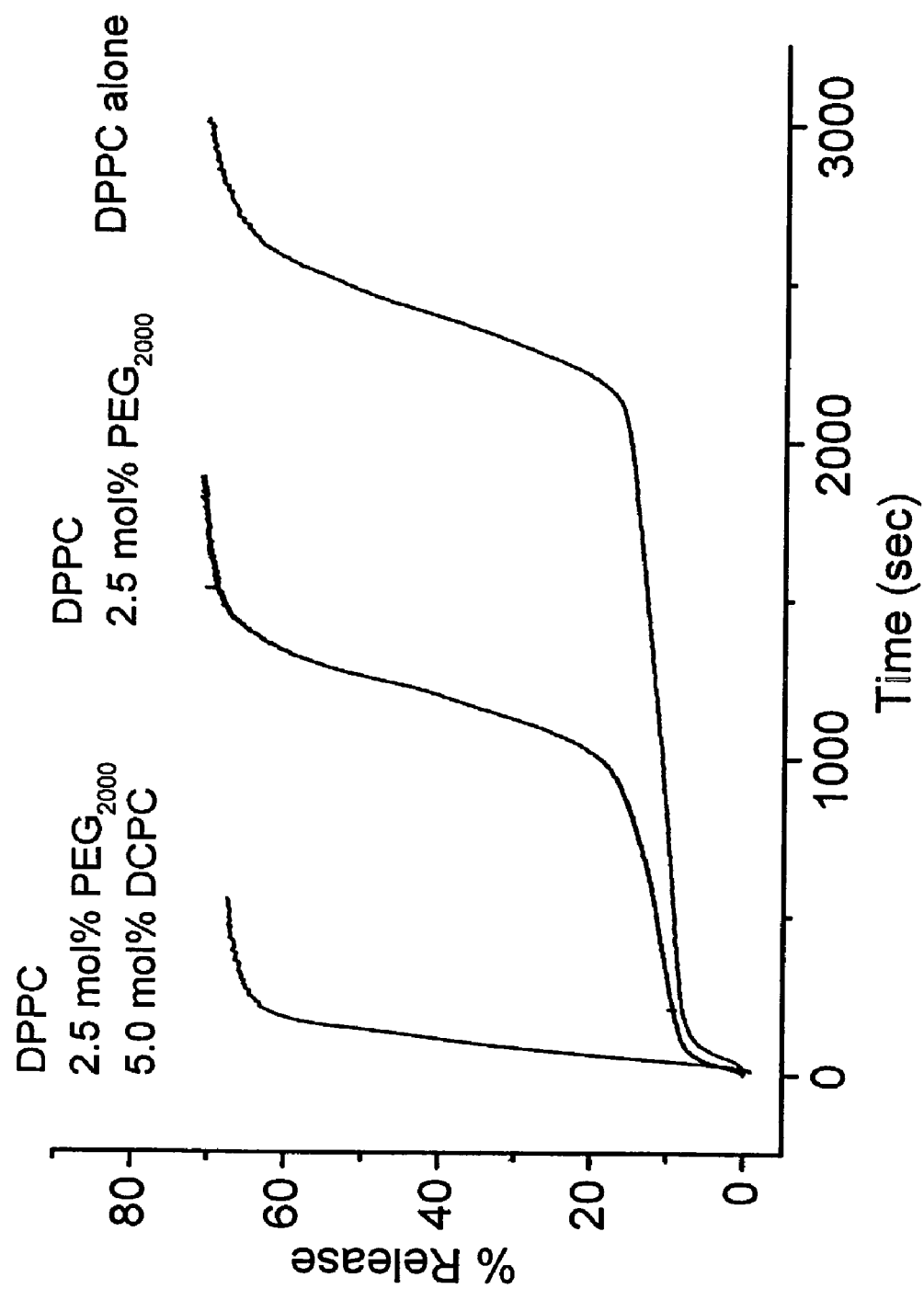

LIPID-BASED SYSTEMS FOR TARGETING DIAGNOSTIC AGENTS

This application is the national phase under 35 U.S.C. §371 of PCT International Application No. PCT/DK01/00269 which has an International filing date of Apr. 11, 2001, which designated the United States of America.

FIELD OF THE INVENTION

The invention relates to targeting of diagnostic agents (herein generally referred to as "labels") by use of lipid-based compositions. The invention is useful in the diagnosis of various disorders which are associated with or resulting from increased levels of extracellular $PLA_2$ activity in the diseased tissue, e.g. cancer, infectious, and inflammatory conditions.

BACKGROUND OF THE INVENTION

Diagnostic imaging is widely used in contemporary medicine. It requires that an appropriate intensity of signal from an area of interest is achieved in order to differentiate certain structures from surrounding tissues, regardless of the technique used. As noted by Torchilin (1998) imaging involves the relationship between the three spatial dimensions of the region of interest and a fourth dimension, time, which relates to both the pharmacokinetics of the agent and the period necessary to acquire the image. The physical properties that can be used to create an image include emission or absorption of radiation, nuclear magnetic moments and relaxation, and transmission or reflection of ultrasound. According to the physical principles applied, currently used imaging techniques include γ-scintigraphy (involving the application of γ-emitting radio-active materials); magnetic resonance (MR, phenomenon based on the transition between different energy levels of atomic nuclei under the action of radiofrequency signal); computed tomography (CT, the technique which utilises ionising radiation with the aid of computers to acquire cross-images of the body and three-dimensional images of areas of interest); and ultra-sonography (US, the technique using irradiation with ultrasound and based on the different rate at which ultrasound passes through various tissues). All four imaging techniques differ in their physical principles, sensitivity, resolution (both spatial and temporal), ability to provide images without contrast agent-mediated enhancement, and some other parameters, such as cost and safety. Usually, the imaging of different organs and tissues for early detection and localisation of numerous pathologies cannot be successfully achieved without appropriate contrast agents (see further) in different imaging procedures.

To improve imaging contrast agents are used. These are the substances which are able to absorb certain types of signal (irradiation) much stronger than surrounding tissues. The contrast agents are specific for each imaging technique (see Table 1), and as a result of their accumulation in certain sites of interest, those sites may be easily visualised when the appropriate imaging technique is applied.

TABLE 1

Imaging techniques and required concentration of diagnostic moieties

| Imaging technique | Diagnostic moiety | Required concentration |
|---|---|---|
| Gamma-scintigraphy | Diagnostic radionuclides, such as $^{111}$In, $^{99m}$Tc, $^{67}$Ga | $10^{-10}$ M |
| Magnetic resonance (MR) imaging | Paramagnetic ions, such as Gd and Mn, and iron oxide | $10^{-4}$ M |
| Computed tomography (CT) imaging | Iodine, bromine, barium | $10^{-2}$ M |
| Ultrasonography | Gas (air, argon, nitrogen) | | from: Torchilin (1998)

The tissue concentration that must be achieved for successful imaging varies between techniques and diagnostic moieties, see table 1. In many cases, contrast agent-mediated imaging is based on the ability of some tissues (i.e., macrophage-rich tissues) to absorb the particulate substances. This process is particle size-dependent and relies on a fine balance between particles small enough to enter the blood or lymphatic capillaries, yet large enough to be retained within the tissue. In any of imaging techniques, two main routes of administration of contrast agent are used: systemic and via local circulation. Each has its own advantages and disadvantages. By varying the physico-chemical properties of a contrast, or contrast carrier, the rate of its disappearance from the injection site upon local administration can be modulated. A disadvantage of systemic administration is that it increases the exposure of non-target organs to potentially toxic contrast agent.

Liposomes

To facilitate the accumulation of contrast in the required zone, various micropartic-ulates have been suggested as carriers for contrast agents. Among those carriers, liposomes, microscopic artificial phospholipid vesicles, draw special attention because of their easily controlled properties and good pharmacological characteristics. Many individual lipids and their mixtures, when suspended in an aqueous phase, spontaneously form bilayered structures (liposomes) in which the hydrophobic parts of their molecules face inwards and the hydrophilic parts are exposed to the aqueous phase surrounding them. Several different types of liposomes exist; each type has specific characteristics and can be prepared by specific methods. Usual classification of liposomes is based on their size and number of concentric bilayers forming a single vesicle (such as multilamellar vesicles (MLV), unilamellar vesicles, LUV, small unilamellar vesicles (SUV)). The methods for producing LUVs can be easily scaled up and used for industrial production of large batches of liposomes with a predictable size and a narrow size distribution.

For almost two decades liposomes have been recognized as promising carriers for drugs and diagnostic agents for the following reasons: (1) Liposomes are completely biocompatible; (2) they can entrap practically any drug or diagnostic agent into either their internal water compartment or into the membrane itself depending on the physico-chemical properties of the drug; (3) liposome-incorporated pharmaceuticals are protected from the inactivating effect of external conditions, yet at the same time do not cause undesirable sidereactions; (4) liposomes also provide a unique opportunity to deliver pharmaceuticals into cells or even inside individual cellular compartments. Pursuing different in vivo delivery purposes, the size, charge and surface properties of liposomes can be easily changed simply by adding new ingredients to the lipid mixture before liposome preparation and/or by variation of preparation methods.

Unfortunately, phospholipid liposomes, if introduced into the circulation, are very rapidly (usual half-clearance time is within 30 min) sequestered by the cells of the reticuloendothelial system (RES). Liver cells are primarily responsible, and the sequestration is relatively dependent on their size, charge, and composition of the liposomes. Circulating peripheral blood monocytes can also endocytose liposomes and later infiltrate tissues and deliver endocytosed liposomes to certain pathological areas in the body.

Until recently, the potential of liposomes as drug carriers has been limited by the rapid clearance of liposomes from the bloodstream. For example, conventional liposomes may be largely cleared from the bloodstream within 1-2 hours after intravenous administration A variety of approaches for extending the circulation time of liposomes have been proposed. Two of these have been successful in extending the half-life of liposomes in the bloodstream by periods of up to 40-50 hours. In one approach, described in U.S. Pat. No. 4,837,028, liposomes are formulated with the ganglioside $G_{M1}$ and predominantly rigid lipids. In another general approach, disclosed in U.S. Pat. No. 5,013,556, liposomes are coated with a layer of polyethylene glycol (PEG) chains.

The imaging of the most macrophage-rich organs of RES, liver and spleen, was the earliest one performed with contrast-loaded liposomes, as RES organs are the natural targets for liposomes and accumulate them well upon intravenous administration. The diagnostic imaging of liver and spleen is usually aimed at discovering tumors and metastases in those organs, as well as certain blood flow irregularities and inflammatory processes. The use of at least three different imaging techniques for this purpose was described, namely, γ-, MR-, and CT-imaging.

Tumor Imaging with Contrast Liposomes

One area of important potential application of contrast-loaded liposomes is tumor imaging. The main mechanism of liposome accumulation in tumors is via extravas-ation through leaky tumor capillaries into the interstitial space. As in many other cases, the efficacy of such accumulation can be sharply increased by using long-circulating PEG-coated liposomes. Liposome-based imaging agents have already been successfully used for γ-, MR-, CT-, and sonographic imaging of tumors. Indium 111 labeled liposomes for tumor imaging (VesCan®, Vestar, Inc.) are already in Phase II-III clinical trials.

Liposome formulations may also be used for visualization of inflammation and infection sites. The use of microparticulate imaging agents for the visualization of infection and inflammation sites is based on the ability of microparticulates to extravasate from the circulation and accumulate in those sites similar to what we already described for tumors and infarcted tissues.

The two major problems connected with the use of liposomes for diagnostic imaging purposes namely low efficacy of contrast liposomes in tumor imaging has often been explained by fast clearance of the liposomes from the blood and their inability to accumulate in the diseased tissue. Both of these obstacles are addressed in the present invention.

BRIEF DESCRIPTION OF THE INVENTION

The present invention is directed to image enhancing systems which are particularly useful in the diagnosis of diseases characterised by localised activity of extracelluar $PLA_2$ activity.

As reported by Kaiser (1999) $PLA_2$ seem to be produced by malignant cells. Immunohistochemical staining of various cancer tissues, including cancer of pancreas, breast and stomach was positive for $PLA_2$. An increased expression and secretion of $PLA_2$ was found in gastric cancer cells stimulated by IL-6, and six out of 16 human carcinoma cell lines spontaneously secreted $PLA_2$ into the culture supernatant (Kaiser, 1999). Thus it seem fairly well established that increased levels of extracellular $PLA_2$ activity are associated with cancer tissue.

The increased $PLA_2$ activity in tumour tissue combined with the observation that liposomes accumulate in tumours via extravasation through leaky tumor capillaries into the interstitial space is basis for the use of liposomes for enhanced imaging of tumors disclosed here.

In addition, extracellular $PLA_2$ activity is elevated in certain diseased regions such as inflammatory and infected tissue. Similar to what is noted with respect to cancer tissue sites, microparticulates have been observed to extravasate from the circulation and accumulate in infected, inflamed and infarcted tissues (Torchilin, 1998). It is however important to note that it is possible to discriminate between infection and tumor using e.g. positively-charged $^{67}Ga$-liposomes which do accumulate in tumors and do not accumulate in infection sites (Ogihara (1986) J Nucl Med 27, 1300-7).

This invention provides such a label delivery system in the form of lipid-based carriers, e.g. liposomes or micelles, composed of lipid-bilayer forming ether-lipids such as glycerophospholipids containing an alkyl-linkage in the 1-position and an acyl-linkage in the sn-2-position on the glycerol backbone and which have polymer or polysaccharide chains grafted thereto. In addition, the carrier system may contain lipid-bilayer stabilising components, e.g. lipopolymers, glycolipids and sterols which lead to an increased vascular circulation time and as a consequence an accumulation in the diseased target tissue. When the carriers reach the target site for the label, e.g. cancer cells, $PLA_2$-catalyzed hydrolysis of the acyl-linkage releases the label, typically lyso-etherlipids and ester-linked derivatives. Contradictory to alkyl-cleavage enzymes which are nearly absent in cancer cells, extracellular $PLA_2$ activity is elevated in cancer tissue. In addition, extracellular $PLA_2$ activity is elevated in diseased regions such as inflammatory tissue.

The present invention provides the use of lipid-based system comprising a lipid derivative and a label, said lipid derivative having (a) an aliphatic group of a length of at least 7 carbon atoms and an organic radical having at least 7 carbon atoms, and (b) a hydrophilic moiety, said lipid derivative furthermore being a substrate for extracellular $PLA_2$ to the extent that the organic radical can be hydrolytically cleaved off, whereas the aliphatic group remains substantially unaffected, whereby lipid derivative from which the organic radical has been cleaved off is liberated in the form of a lysolipid derivative which is not a substrate for lysophospholipase, said system having included therein lipopolymers or glycolipids so as to present hydrophilic chains on the surface of the system, for the preparation of a diagnostic composition for detecting and/or quantifying diseases or conditions associated with a localised increase in extracellular $PLA_2$ activity in mammalian tissue.

Thus, the present invention takes advantage of the surprising finding that liposomes (and micelles) including lipid derivatives which can be specifically and only partially cleaved by extracellular phospholipases, and which at the same time includes lipopolymers or glycolipids, have the properties of circulating in the blood stream sufficiently long so as to reach target tissue where the extracellular PLA$_2$ activity is elevated without being recognised by the mammalian reticuloendothelial systems and without penetrating cell walls, whereby the lipid derivatives of the liposomes are specifically cleaved by extracellular PLA$_2$ so as to liberate image enhancing ingredients at the desired location.

DESCRIPTION OF THE DRAWINGS

FIG. 1. Heat capacity curves obtained using differential scanning calorimetry. (a) Multilamellar, MLV (the upper curve) and unilamellar, LUV (the bottom curve) liposomes made of 1 mM 1-O-hexadecyl-2-hexadecanoyl-sn-glycero-3-phosphocholine (1-O-DPPC). (b) MLV (the upper curve) and LUV (the bottom curve) liposomes made of dipalmitoylphosphatidylcholine (DPPC).

(I) Pathological tissue with leaky capillaries
(II) Liposomal drug and/or contrast agent carrier
(III) Target cell and cell membrane
(IV) Localised drug and/or contrast agent release and absorption by extracellular phospholipase A2.

Figure 11A:
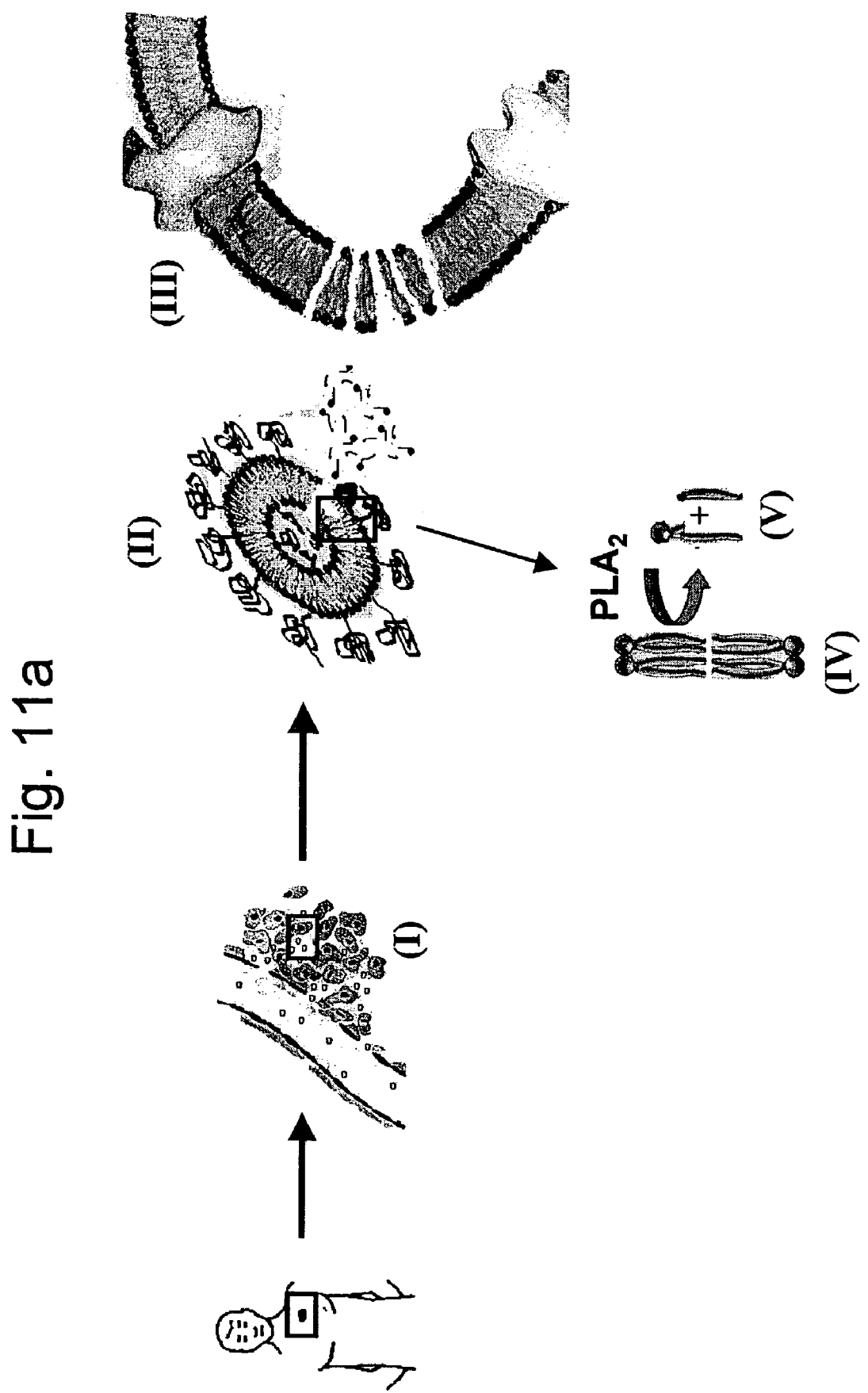

FIG. 11(*a*). Schematic illustration of the liposomal drug and/or contrast agent targeting principle involving accumulation of the liposomal drug and/or contrast agent drug carriers in porous diseased tissue and subsequent release of drug and/or contrast agent and transport across the target membrane via extracellular PLA$_2$ activity.
(I) Pathological tissue with leaky capillaries
(II) Polymer-stabilised lipid-conjugated contrast agents contrast agent carrier liposome
(III) Target cell and cell membrane
(IV) Lipid-conjugated contrast agents (monoether-lipid), proenhancer (lipid), proactivator (lipid)
(V) Drugs (ether-lysolipid and fatty acid derivatives), enhancers (lysolipid+fatty acid), PLA$_2$ activators (lysolipid+fatty acid)

FIG. 11(b) Schematic illustration of a molecular-based biophysical model system where the phospholipids of the drug and/or contrast agent carrier liposomes, via the PLA$_2$-catalysed hydrolysis, act as prodestabilisers at the site of the drug and/or contrast agent carrier and as proenhancers at the site of the target. The possibility of extending the principle to include a lipid-based lipid-conjugated contrast agents is also included.
(I) Polymer stabilised drug and/or contrast agent carrier liposome
(II) Non-degradable target liposomal membrane
(III) Non-hydrolysable ether-lipids
(IV) Proenhancer (lipid), lipid-conjugated contrast agents (monoether-lipid), proactivator (lipid)
(V) Enhancers (lysolipid+fatty acid), drugs (ether-lysolipid and fatty acid derivatives), PLA$_2$ activators (lysolipid+fatty acid)

Figure 12B:
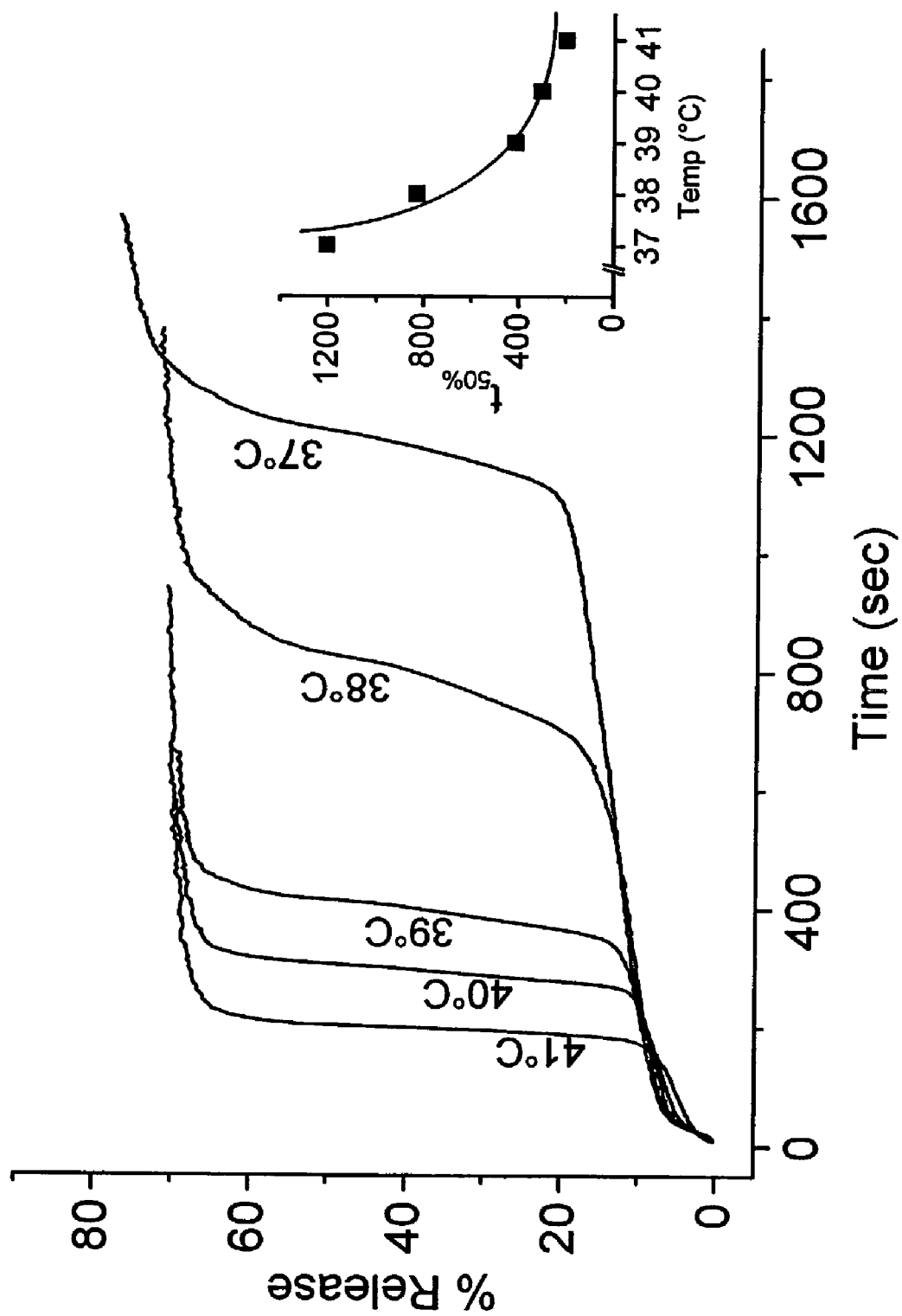

FIG. 12(a) PLA$_2$-controlled release of the fluorescent model drug and/or calcein across the target membrane as a function of time for different compositions of the carrier liposomes. The temperature is 37° C. In comparison with bare DPPC carriers, the rate of release of the model drug and/or contrast agent is dramatically enhanced for the polymer-coated carriers, DPPC+2.5 mol % DPPE-PEG2000. A further augmentation of the rate of release is obtained if the carrier also contains a short-chain phospholipid, DCPC, which acts as a local activator for the enzyme. The percentage of calcein released is determined as % Release=100 $(I_{F(t)}-I_B)/(I_T-I_B)$, where $I_{F(t)}$ is the measured fluorescence at time t after addition of the enzyme, $I_B$ is the background fluorescence, and $I_T$ is the total fluorescence measured after addition of Triton X-100 which leads to complete release of calcein by breaking up the target liposomes. (b) PLA$_2$-controlled release of the fluorescent model drug and/or contrast agent calcein across the target membrane as a function of time for different temperatures. As the temperature is raised, the rate of release is enhanced due to increased activity of the enzyme induced by structural changes in the lipid bilayer substrate of the carrier liposome. In the present assay a maximum release of about 70% is achieved in all cases. The insert shows the time of 50% calcein release, $t_{50\%}$, as a function of temperature. The concentration of the target and carrier liposomes are 25 µM, and PLA$_2$ is added in a 25 nM concentration in a HEPES buffer with pH=7.5.

Figure 13:
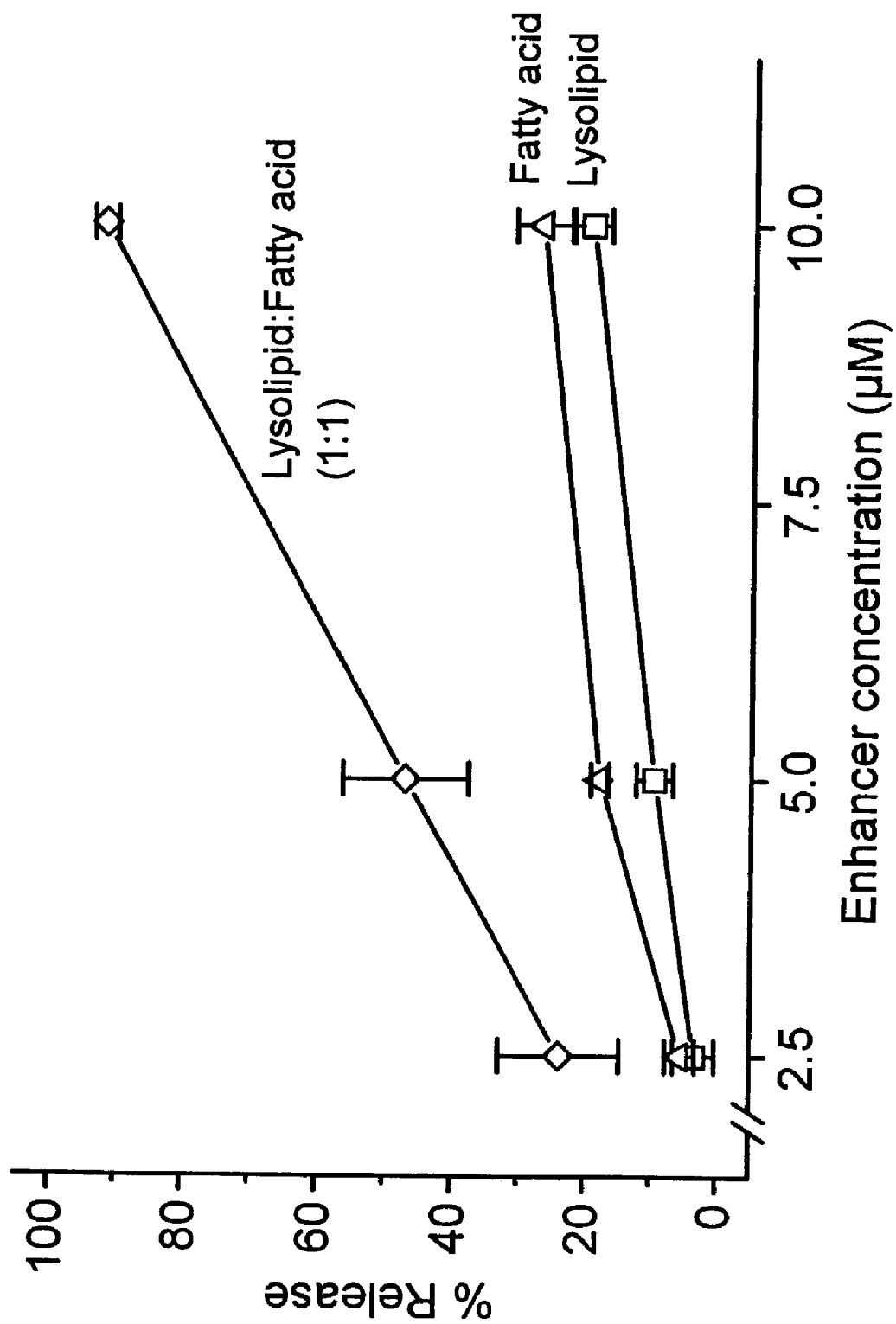

FIG. 13. Total release after 20 min of the fluorescent model drug and/or contrast agent calcein across the target membrane as a function of adding increasing amounts of lyso-palmitoyl phospholipid and palmitic acid, separately, and in a 1:1 mixture. The concentration of the target membranes is 25 µM in a HEPES buffer with pH=7.5 at a temperature of 39° C.

Figure 14:
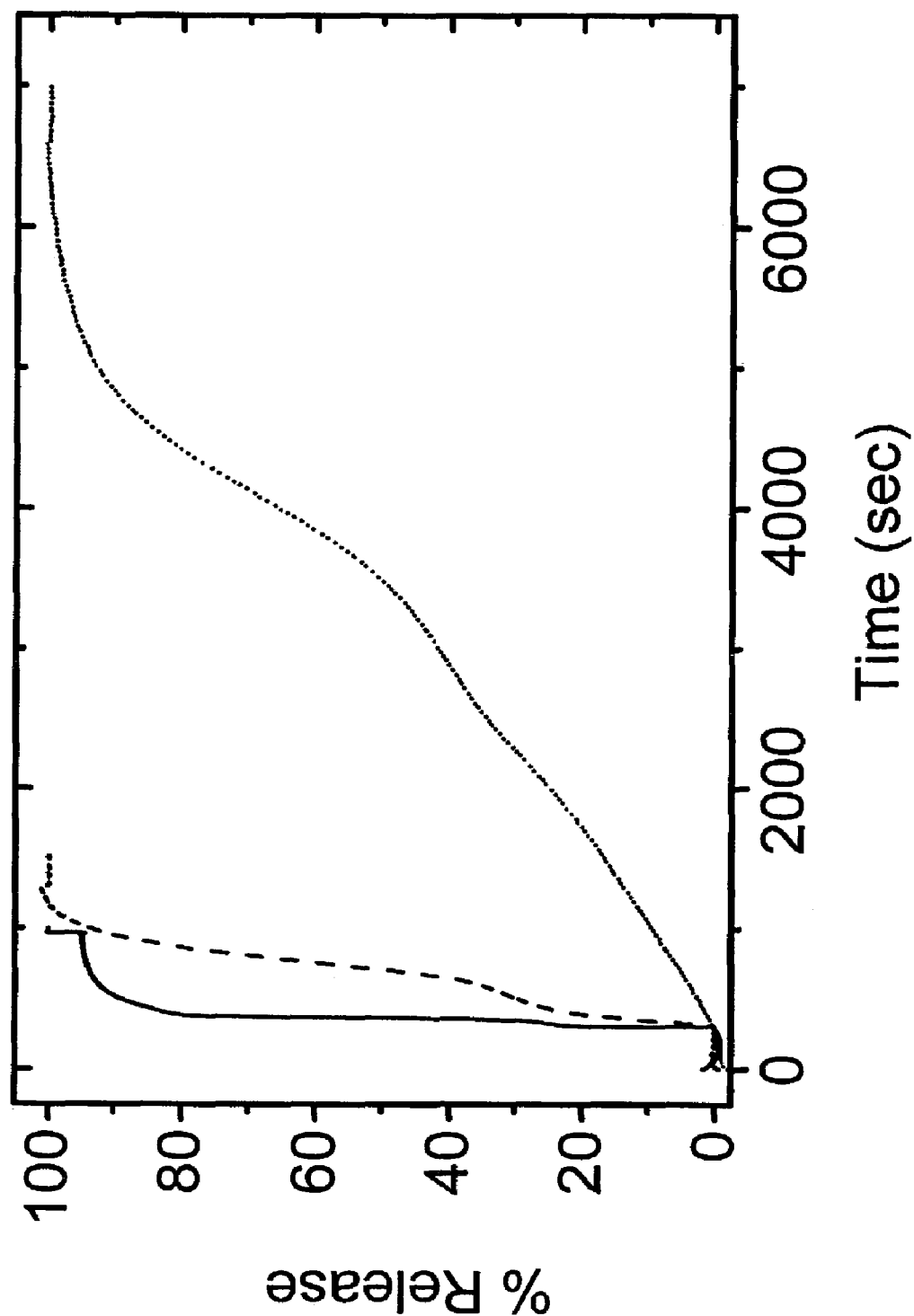

FIG. 14. PLA$_2$-controlled release of the fluorescent model drug and/or contrast agent calcein from liposomes composed of 25 µM 90 mol % 1-O-hexadecyl-2-hexadecanoyl-sn-glycero-3-phosphocholine (1-O-DPPC) and 10 mol % 1-O-hexadecyl-2-hexadecanoyl-sn-glycero-3-phosphoethanolamine-N-[methoxy(polyethylene glycol)-350] (1-O-DPPE-PEG350) suspended in a 10 mM HEPES-buffer (pH=7.5), as a function of time. 50 nM (straight line), 1 nM (solid line) and 0.02 nM (dotted line) phospholipase A$_2$ (A. piscivorus piscivorus) was added at time 300 sec, the temperature was 35.5° C. The percentage of calcein released is determined as describe in FIG. 4.

Figure 15:
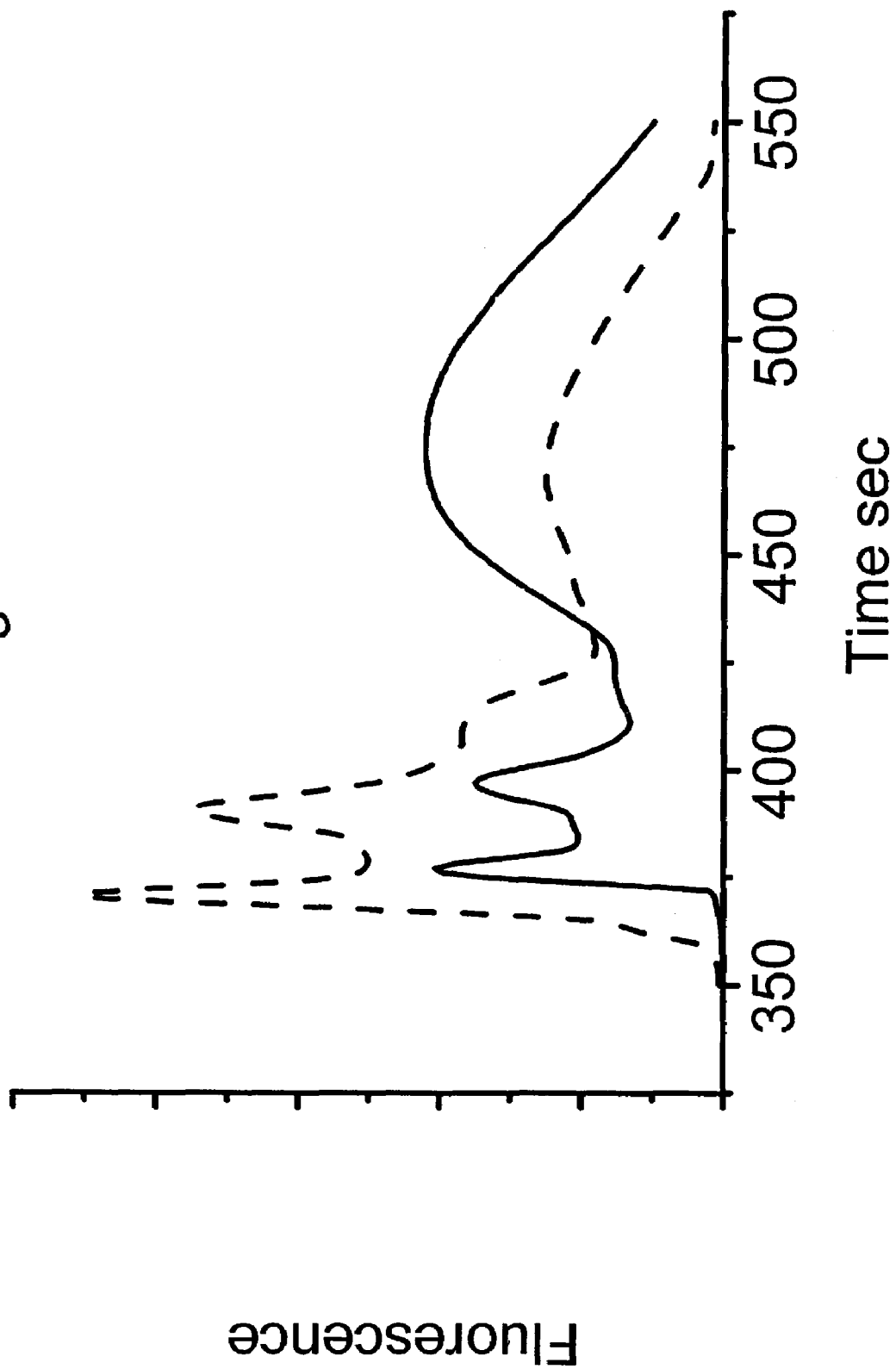

FIG. 15. Emission spectrum of 1 mol % bis-py-DPC incorporated into negatively charged liposomes (0.100 mM) before (solid line) and after (dashed line) adding 100 nM PLA$_2$ (Agkistrodon piscivorus piscivorus) to a liposome suspension equilibrated at 41° C.

Figure 16:
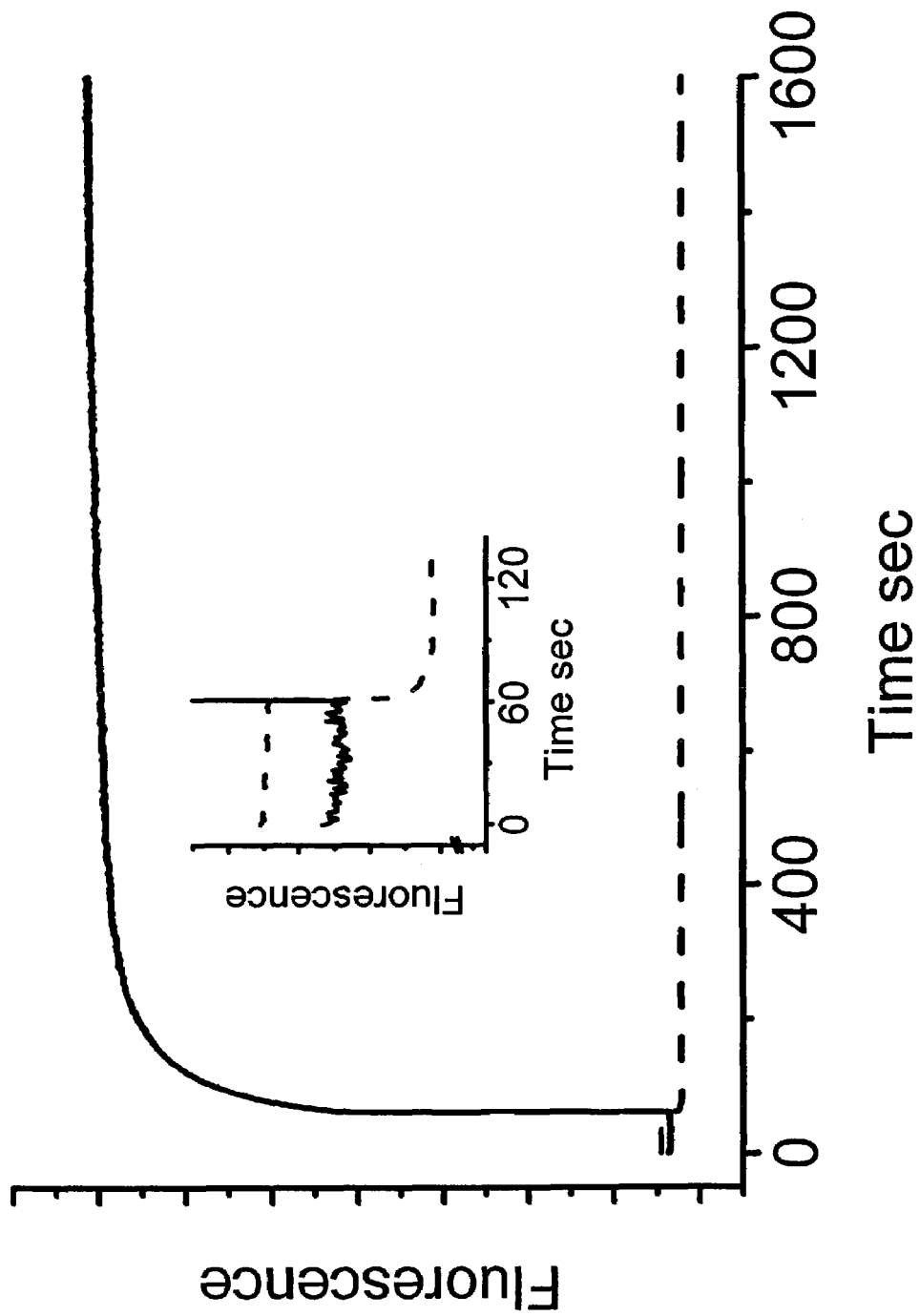

FIG. 16. Characteristic reaction time profile at 41° C. for rat phospholipase catalysed hydrolysis of negatively charged liposomes. The catalytic reaction was initiated by adding cell-free peritoneal fluid to 2.5 ml of the thermostated liposome suspension equilibrated for 60 sec prior to addition of peritoneal fluid. The hydrolysis reaction is monitored by monomer fluorescence (solid line) and eximer fluorescence (dashed line) from bis-py-DPC. After adding undiluted peritoneal fluid, at 60 sec, to the equilibrated liposome suspension a sudden increase in monomer fluorescence, and a simultaneously decrease in eximer fluorescence is observed as the bis-py-DPC substrate is hydrolysed. The insert shows the reaction time profile of the first 120 sec.

DETAILED DESCRIPTION OF THE INVENTION

One of the important features of the present invention is the realisation that certain lipid derivatives will be cleaved by extracellular PLA$_2$ in a well-defined manner in specific extracellular locations of mammalian tissue. It has been found that extracellular PLA$_2$ is capable of cleaving monoether/monoester lipid derivatives so as to target the label in relevant diseased tissue.

Lipid Derivatives

Thus, the image enhancing systems (liposomes or micelles) for use in the present invention relies on lipid derivative having (a) an aliphatic group of a length of at least 7 carbon atoms and an organic radical having at least 7 carbon atoms, and (b) a hydrophilic moiety, said lipid-conjugated contrast agents furthermore being a substrate for extracellular phospholipase A2 to the extent that the organic radical can be hydrolytically cleaved off, whereas the aliphatic group remains substantially unaffected, whereby the lipid-conjugated contrast agents is liberated in the form of a lysolipid derivative which is not a substrate for lysophospholipase, said system having included therein lipopolymers or glycolipids so as to present hydrophilic chains on the surface of the system.

Although the terms "lipid" and "lysolipid" (in the context of phospholipids) will be well-known terms for the person skilled in the art, it should be emphasised that, within the present description and claims, the term "lipid" is intended to mean triesters of glycerol of the following formula:

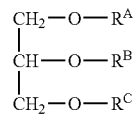

wherein $R^A$ and $R^B$ are fatty acid moieties ($C_{9-30}$-alkyl/alkylene/alkyldiene/alkyltriene/-alkyltetraene-C(=O)—)

and $R^C$ is a phosphatidic acid ($PO_2$—OH) or a derivative of phosphatidic acid. Thus, the groups $R^A$ and $R^B$ are linked to the glycerol backbone via ester bonds.

The term "lysolipid" is intended to mean a lipid where the $R^B$ fatty acid group is absent (e.g. hydrolytically cleaved off), i.e. a glycerol derivative of the formula above where $R^B$ is hydrogen, but where the other substituents are substantially unaffected. Conversion of a lipid to a lysolipid can take place under the action of an enzyme, specifically under the action of cellular as well as extracellular $PLA_2$.

The terms "lipid derivative" and "lysolipid derivative" are intended to cover possible derivatives of the above possible compounds within the groups "lipid" and "lysolipid", respectively. Examples of biologically active lipid derivatives and lysolipid derivatives are given in Houlihan, et al., Med. Res. Rev., 15, 3, 157-223. Thus, as will be evident, the extension "derivative" should be understood in the broadest sense.

Within the present application, lipid derivatives and lysolipids should however fulfil certain functional criteria (see above) and/or structural requirements. It is particularly relevant to note that the suitable lipid derivatives are those which have (a) an aliphatic group of a length of at least 7, preferably at least 9, carbon atoms and an organic radical having at least 7 carbon atoms, and (b) a hydrophilic moiety. It will be evident that the aliphatic group and the organic radical will correspond to the two fatty acid moieties in a normal lipid and that the hydrophilic moiety will correspond to the phosphate part of a (phospho)lipid or a bioisoster thereof.

Thus, as the general idea behind the present invention is to exploit the increased level of extracellular $PLA_2$ activity in localised areas of the body of a mammal, in particular diseased tissue, the lipid derivatives which can be utilised within the present invention should be substrates for extracellular $PLA_2$, i.e. the lipid derivatives should be able to undergo hydrolytic, enzymatic cleavage of the organic radical corresponding to the fatty acid in the 2-position in a lipid. Extracellular $PLA_2$ is known to belong to the enzyme class (EC) 3.1.1.4. Thus by reference to (extracellular) $PLA_2$ should be understood all extracellular enzymes of this class, e.g. lipases, which can induce hydrolytic cleavage of the organic radical corresponding to the fatty acid in the 2-position in a lipid. One particular advantage of the lipid based image enhancing system (as liposomes and micelles) is that extracellular $PLA_2$ activity is significantly increased towards organised substrates as compared to monomeric substrates.

In view of the requirement to hydrolysability by extracellular $PLA_2$, it is clear that the organic radical (e.g. aliphatic group) is preferably linked via an ester functionality which can be cleaved by extracellular $PLA_2$, preferably so that the group which is cleaved off is a carboxylic acid.

Furthermore, it is an important feature of the present invention that the aliphatic group (the group corresponding to the fatty acid in the 1-position in a lipid) of the lipid derivative, i.e. the lysolipid derivative after cleavage by extracellular $PLA_2$, is substantially unaffected by the action of extracellular $PLA_2$. By "substantially unaffected" is meant that the integrity of the aliphatic group is preserved and that less than 1 mol %, preferably less than 0.1 mol %, of the aliphatic group (the aliphatic group in the 1-position) is is cleaved under the action of extracellular $PLA_2$.

Also, the lysolipid derivative resulting from the hydrolytic cleavage of the organic radical should not in itself be a substrate for lysophospholipase. Lysophospholipase is known to belong to the enzyme class (EC) 3.1.1.5. Thus by reference to lysophospholipase should be understood all enzymes of this class that catalyses the reaction lyso(phospho)lipid+water yielding phosphoglycerol+fatty acid. The term "not a substrate for lysophospholipase" is intented to mean that lysophospholipase has an activity of less than 1% towards the substrate compared with the corresponding esterlipid, i.e. virtually not enzymatic activity.

Suitable examples of such lysolipid derivatives are those which will not undergo hydrolytical cleavage under the action of lysophospholipases. Thus, the lysolipid derivatives are in particular not lysolipids and lysolipid derivatives which have an ester linkage in the 1-position of the lysolipid or the position of a lysolipid derivative which corresponding to the 1-position of a lysolipid.

One preferred class of lipid derivatives for incorporation in the image enhancing systems of the invention can be represented by the following formula:

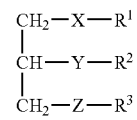

wherein
X and Z independently are selected from O, $CH_2$, NH, NMe, S, S(O), and $S(O)_2$, preferably from O, NH, NMe and $CH_2$, in particular O;
Y is —OC(O)—, Y then being connected to $R^2$ via either the oxygen or carbonyl carbon atom, preferably via the carbonyl carbon atom;
$R^1$ is an aliphatic group of the formula $Y^1Y^2$;
$R^2$ is an organic radical having at least 7 carbon atoms, such as an aliphatic group having a length of at least 7, preferably at least 9, carbon atoms, preferably a group of the formula $Y^1Y^2$;
where $Y^1$ is —$(CH_2)_{n1}$—(CH=CH)$_{n2}$—$(CH_2)_{n3}$—(CH=CH)$_{n4}$—$(CH_2)_{n5}$—(CH=CH)$_{n6}$—$(CH_2)_{n7}$—(CH=CH)$_{n8}$—$(CH_2)_{n9}$, and the sum of n1+2n2+n3+2n4+n5+2n6+n7+2n8+n9 is an integer of from 9 to 29; n1 is zero or an integer of from 1 to 29, n3 is zero or an integer of from 1 to 20, n5 is zero or an integer of from 1 to 17, n7 is zero or an integer of from 1 to 14, and n9 is zero or an integer of from 1 to 11; and each of n2, n4, n6 and n8 is independently zero or 1; and $Y^2$ is $CH_3$ or $CO_2H$; where each $Y^1$-$Y^2$ independently may be substituted with halogen or $C_{1-4}$-alkyl, but preferably $Y^1$-$Y^2$ is unsubstituted,
$R^3$ is selected from phosphatidic acid ($PO_2$—OH), derivatives of phosphatidic acid and bioisosters to phosphatic acid and derivatives thereof (among others phosphatidic acid derivatives to which a hydrophilic polymer or polysaccharide is covalently attached).

As mentioned above, preferred embodiments imply that Y is —OC(O)— where Y is connected to $R^2$ via the carboxyl atom. The most preferred embodiments imply that X and Z are O and that Y is —OC(O)— where Y is connected to $R^2$ via the carboxyl atom. This means that the lipid derivative is a 1-monoether-2-monoester-phospholipid type compound.

Another preferred group of lipid derivatives is the one where the group X is S.

In one embodiment, $R^1$ and $R^2$ are aliphatic groups of the formula $Y^1 Y^2$ where $Y^2$ is $CH_3$ or $CO_2H$, but preferably $CH_3$, and where $Y^1$ is —$(CH_2)_{n1}$(CH=CH)$_{n2}$$(CH_2)_{n3}$(CH=CH)$_{n4}$—$(CH_2)_{n5}$(CH=CH)$_{n6}$$(CH_2)_{n7}$(CH=CH)$_{n8}$$(CH_2)_{n9}$; the sum of n1+2n2+n3+2n4+n5+2n6+n7+2n8+n9 is an integer of from 9 to 23; that is, the aliphatic group, $Y^1Y^2$, is from 10-24 carbon atoms in length. n1 is equal to zero or is an integer of from 1 to 23; n3 is equal to zero or is an integer of from 1 to 20; n5 is equal to zero or is an integer of from 1 to 17; n7 is equal to zero or is an integer of from 1 to 14; n9 is equal to zero or is an integer of from 1 to 11; and each of n2, n4, n6 and 8 is independently equal to zero or 1.

In one embodiment, one or more of the aliphatic groups $R^1/R^2$ or the $R^3$ groups include a label, e.g. halogens (bromo, iodo) or barium atoms which are particular suitable for computed tomography (CT) imaging, or are enriched with unstable isotopes, e.g. $^{11}C$ which is particularly useful for PET scanning purposes.

The aliphatic groups as $R^1$ and $R^2$ are in one embodiment preferably saturated as well as unbranched, that is, they preferably have no double bonds between adjacent carbon atoms, each of n2, n4, n6 and n8 then being equal to zero. Accordingly, $Y^1$ is preferably $(CH_2)_{n1}$. More preferably (in this embodiment), $R^1$ and $R^2$ are each independently $(CH_2)_{n1}CH_3$, and most preferably, $(CH_2)_{17}CH_3$ or $(CH_2)_{15}CH_3$. In alternative embodiments, the groups can have one or more double bonds, that is, they can be unsaturated, and one or more of n2, n4, n6 and n8 can be equal to 1. For example, when the unsaturated hydrocarbon has one double bond, n2 is equal to 1, n4, n6 and n8 are each equal to zero and $Y^1$ is $(CH_2)_{n1}$ CH=CH$(CH_2)_{n3}$. n1 is equal to zero or is an integer of from 1 to 21, and n3 is also zero or is an integer of from 1 to 20, at least one of n1 or n3 not being equal to zero.

In one particular embodiment, the lipid derivatives are those which are monoether lipids where X and Z are O, $R^1$ and $R^2$ are independently selected from alkyl groups, $(CH_2)_n$ $CH_3$, where n is 11, 12, 13, 14, 15, 16, 17, 18, 19, 20, 21, 22, 23, 24, 25, 26, 27, 28, or 29, preferably 14, 15 or 16, in particular 14; Y is —OC(O)—, Y then being connected to $R^2$ via the carbonyl carbon atom.

With respect to the hydrophilic moiety (often known as the "head group") which corresponds to $R^3$, it is believed that a wide variety of groups corresponding to phosphatidic acid ($PO_2$—OH), derivatives of phosphatidic acid and bioisosters to phosphatic acid and derivatives thereof can be used. As will be evident, the crucial requirement to $R^3$ is that the groups should allow for enzymatic cleavage of the $R^2$ group (actually $R^2$—C(=O) or $R^2$—OH) by extracellular $PLA_2$. "Bioisosters to phosphatidic acid and derivatives thereof" indeed implies that such groups—as phosphatidic acid—should allow for enzymatic cleavage by extracellular $PLA_2$.

$R^3$ is typically selected from phosphatidic acid ($PO_2$—OH), phosphatidylcholine ($PO_2$—O—$CH_2CH_2N(CH_3)_3$), phosphatidylethanolamine ($PO_2$—O—$CH_2CH_2NH_2$), N-methyl-phosphatidylethanolamine ($PO_2$—O—$CH_2CH_2NCH_2$), phosphatidylserine, phosphatidylinositol, and phosphatidylglycerol ($PO_2$—O—$CH_2CHOHCH_2OH$). Other possible derivatives of phosphatidic acid are those where dicarboxylic acids, such as glutaric, sebacic, succinic and tartaric acids, are coupled to the terminal nitrogen of phosphatidyl-ethanolamines, phosphatidylserine, phosphatidylinositol, etc.

In the particular embodiment where a fraction of the lipid derivative also is a lipopolymer or glycolipid, a hydrophilic polymer or polysaccharide is typically covalently attached to the phosphatidyl part of the lipid derivative.

Hydrophilic polymers which suitable can be incorporated in the lipid derivatives of the invention so as to form lipopolymers are those which are readily water-soluble, can be covalently attached to a vesicle-forming lipid, and which are tolerated in vivo without toxic effects (i.e. are biocompatible). Suitable polymers include polyethylene glycol (PEG), polylactic (also termed polylactide), polyglycolic acid (also termed polyglycolide), a polylactic-polyglycolic acid copolymer, polyvinyl alcohol, polyvinylpyrrolidone, polymethoxazoline, polyethyloxazoline, polyhydroxypropyl methacrylamide, polymethacrylamide, polydimethylacrylamide, and derivatised celluloses such as hydroxymethylcellulose or hydroxyethylcellulose.

Preferred polymers are those having a molecular weight of from about 100 daltons up to about 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilises polymers of at least about three monomers, such PEG polymers consisting of three monomers (approximately 150 daltons).

When the glycolipid or lipopolymer is represented by a fraction of the lipid derivative, such a lipid derivative (lipid derivative with a polymer or polysaccharide chain) typically constitutes 1-80 mol %, such as 2-50 mol % or 3-25 mol % of the total dehydrated lipid-based system. For micellular compositions, however, the fraction may be even higher, such as from 1-100 mol %, such as 10-100 mol %, of the total dehydrated lipid-based system.

Preferred polymers to be covalently linked to the phosphatidyl part (e.g. via the terminal nitrogen of phosphatidylethanolamine) are polyethylene glycol (PEG), polyactide, polyglycolic acid, polyactide-polyglycolic acid copolymer, and polyvinyl alcohol.

It should be understood that $R^2$ should be an organic radical having at least 7 carbon atoms) (such as an aliphatic group having a certain length (at least 7, preferably 9, carbon atoms)), a high degree of variability is possible, e.g. $R^2$ need not necessarily to be a long chain residue, but may represent more complex structures.

Generally, it is believed that $R^2$ may either be rather inert for the environment in which it can be liberated by extracellular $PLA_2$ or that $R^2$ may present a label suitable for the diagnostic application. Alternatively, $R^2$ may play an active pharmaceutical role, typically as an auxiliary drug substance or as an efficiency modifier for the lysolipid derivative and/or any other (second) drug substances present in the environment. In the latter instance, the lipid based system may have a therapeutic effect as well as the useful properties with respect to the diagnostic method. In this embodiment, the group $R^2$ may be a long chain residue, e.g. a fatty acid residue (the fatty acid will include a carbonyl from the group Y). This has been described in detail above. Interesting examples of auxiliary drug substances as $R^2$ within these subgroups are polyunsaturated acids, e.g. oleate, linoleic, linolenic, as well as derivatives of arachidonoyl (including the carbonyl from Y), e.g. prostaglandins such as prostaglandin $E_1$, as arachidonic acid derivatives are know regulators of hormone action including the action of prostaglandins, thromboxanes, and leukotrines. Examples of efficiency modifiers as $R^2$ are those which enhance the permeability of the target cell membrane as well as enhances the activity of extracellular $PLA_2$ or the lipid-conjugated contrast agents or any second drug substances. Examples hereof are short chain $(C_{8-12})$ fatty acids.

Thus, the present invention also relates to the use of the lipid-based system for simultaneous diagnostic and therapeutic purposes.

It should be understood that the various examples of possible $R^2$ groups are referred to by the name of a discrete species, rather than the name of the radical. Furthermore, it should be understood that the possible examples may include the carbonyl group or oxy group of the bond via which the organic radical is linked to the lipid skeleton (corresponding to "Y" in the formula above). This will of course be appreciated by the person skilled in the art.

Even though it has not specifically been indicated in the general formula for the suitable examples of lipid derivatives to be used within the present invention, it should be understood that the glycol moiety of the lipid derivatives may be substituted, e.g. in order to modify the cleavage rate by extracellular $PLA_2$ or simply in order to modify the properties of the liposomes comprising the lipid derivatives.

A particular group of useful compounds for the lipid-bases system is lipid derivatives of the following formula:

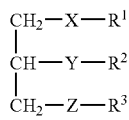

wherein

X and Z independently are selected from O, $CH_2$, NH, NMe, S, S(O), and $S(O)_2$, preferably from O, NH, NMe and $CH_2$, in particular O;

Y is —OC(O)—, Y then being connected to $R^2$ via either the oxygen or carbonyl carbon atom, preferably via the carbonyl carbon atom;

$R^1$ is an aliphatic group of the formula $Y^1Y^2$;

$R^2$ is an organic radical having at least 7 carbon atoms;

where $Y^1$ is —$(CH_2)_{n1}$—$(CH=CH)_{n2}$—$(CH_2)_{n3}$—$(CH=CH)_{n4}$—$(CH_2)_{n5}$—$(CH=CH)_{n6}$—$(CH_2)_{n7}$—$(CH=CH)_{n8}$—$(CH_2)_{9n}$, and the sum of n1+2n2+n3+2n4+n5+2n6+n7+2n8+n9 is an integer of from 9 to 29; n1 is zero or an integer of from 1 to 29, n3 is zero or an integer of from 1 to 20, n5 is zero or an integer of from 1 to 17, n7 is zero or an integer of from 1 to 14, and n9 is zero or an integer of from 1 to 11; and each of n2, n4, n6 and n8 is independently zero or 1; and $Y^2$ is $CH_3$ or $CO_2H$; where each $Y^1$-$Y^2$ independently may be substituted with halogen or $C_{1-4}$-alkyl, but preferably $Y^1$-$Y^2$ is unsubstituted, $R^3$ is selected from derivatives of phosphatidic acid to which a hydrophilic polymer or polysaccharide is attached. The hydrophilic polymer or polysaccharide is typically and preferably selected from polyethylene glycol, poly(lactic acid), poly(glycolic acid), poly(lactic acid)-poly(glycolic acid) copolymers, polyvinyl alcohol, polyvinylpyrrolidone, polymethoxazoline, polyethyloxazoline, polyhydroxypropyl methacrylamide, polymethacrylamide, polydimethylacrylamide, and derivatised celluloses, in particular from polyethylene glycol, poly(lactic acid), poly(glycolic acid), poly(lactic acid)-poly(glycolic acid) copolymers, and polyvinyl alcohol.

Particular subgroups are those wherein X and Z are O, $R^1$ and $R^2$ are independently selected from alkyl groups, $(CH_2)_n CH_3$, where n is 11, 12, 13, 14, 15, 16, 17, 18, 19, 20, 21, 22, 23, 24, 25, 26, 27, 28, or 29, preferably 14 or 16; Y is —OC(O)—, Y then being connected to $R^2$ via the carbonyl carbon atom.

A specific group of compounds are polyethyleneoxide-1-O-palmityl-sn-2-palmitoyl-phosphatidyl ethanolamine, DPPE-PEG, and polyethyleneoxide-1-O-stearyl-sn-2-stearoyl-phosphatidylethanolamine, DSPE-PEG, with PEG molecular weight from 100 to 10000 Daltons, in particular from 300-5000 Daltons.

Lipid Derivatives Formulated as Liposomes and Micelles

The term "lipid-based image enhancing system" encompass macromolecular structures which as the main constituent include lipid or lipid derivatives. Suitable examples hereof are liposomes and micelles. It is presently believed that liposomes offer the broadest scope of applications and those have been described most detailed in the following. Although liposomes currently are believed to be the preferred lipid-based system, micellular systems are also believed to offer interesting embodiments within the present invention.

In one important variant which advantageously can be combined with the embodiments described herein, the lipid derivative is included in liposomes either as the only constituent or—which is more common—in combination with other constituents (other lipids, sterols, etc.). Thus, the lipid-based systems described herein are preferably in the form of liposomes, wherein the liposomes are build up of layers comprising the lipid derivative and the label.

When used herein, the term "label" is intended to mean a species which is capable of being administered to the mammalian body and being detected by extracorporal means for imaging living tissue. The label may be selected from radiolabels such as radioisotopes and radioisotope-labeled compounds; radiopaque compounds; fluorescent compounds, etc. More specific labels are $^{111}In$, $^{99m}Tc$, $^{67}Ga$, $^{11}C$; Gd, Mn, iron oxide, argon, nitrogen, Iodine, bromine and barium.

Suitable labels for gamma-scintigraphy are diagnostic radionuclides, such as $^{111}In$, $^{99m}Tc$, $^{67}Ga$. For practical purposes the radionucleotides are complexed with e.g. chelators such as diethylene triamine pentaacetic acid (DTPA), hexamethylpropyleneamine oxime (HMPAO), diisopropyl iminodiacetic acid (DISIDA), or even proteins such as human serum albumin (HSA). Alternatively DTPA or similar chelating compounds may be derivatized by the incorporation of a hydrophobic group, which can anchor the chelating moiety on the liposome surface during or after liposome preparation.

Suitable labels for X-ray are verografin, ioxaglate, iohexol, iopromide, iomeprol, iopamidol, iopentol, iodixanol, ioversol different nonionic contrast media, etc. which may be incorporated in liposomes and used both for planar X-ray imaging of the liver and spleen and for CT imaging.

Suitable labels for magnetic resonance (MR) imaging are paramagnetic ions, such as Gd and Mn, and iron oxide coupled to various carrier molecules. E. g. gadolinium diethylenetriamine pentaacetic acid (Gd-DTPA) complex has been demonstrated to be effective contrast agents for MR imaging of liver, spleen, and hepatic metastases.

Suitable labels for computed tomography (CT) imaging are iodine, bromine, barium, etc.

Other examples of suitable labels are often given by the selected method of imaging or detection, examples of which are described in detail in Handbook of medical imaging, vol. 1, 2, 3, SPIE Press, Washington USA, 2000, edd. Beutel, Konden and van Metter.

"Liposomes" are known as self-assembling structures comprising one or more lipid bilayers, each of which surrounds an aqueous compartment and comprises two opposing monolayers of amphipathic lipid molecules. Amphipathic lipids (herein i.a. lipid derivatives) comprise a polar (hydrophilic) headgroup region (corresponding to the substituent $R^3$ in the lipid derivatives) covalently linked to one or two non-polar (hydrophobic) aliphatic groups (corresponding to $R^1$ and $R^2$ in the lipid derivatives). Energetically unfavourable contacts between the hydrophobic groups and the aqueous medium are generally believed to induce lipid molecules to rearrange such that the polar headgroups are oriented towards the aqueous medium while the hydrophobic groups reorient towards the interior of the bilayer. An energetically stable structure is formed in which the hydrophobic groups are effectively shielded from coming into contact with the aqueous medium.

As will be understood from the above, the lipid-bases systems, e.g. liposomes, are particularly useful for incorporation of labels.

Liposomes can have a single lipid bilayer (unilamellar liposomes, "ULVs"), or multiple lipid bilayers (multilamellar liposomes, "MLVs"), and can be made by a variety of methods (for a review, see, for example, Deamer and Uster, Liposomes, Marcel Dekker, N.Y., 1983, 27-52). These methods include Bangham's methods for making multilamellar liposomes (MLVs); Lenk's, Fountain's and Cullis' methods for making MLVs with substantially equal interlamellar solute distribution (see, e.g., U.S. Pat. No. 4,522,803, U.S. Pat. No. 4,588,578, U.S. Pat. No. 5,030,453, U.S. Pat. No. 5,169,637 and U.S. Pat. No. 4,975,282); and Papahadjopoulos et al.'s reverse-phase evaporation method (U.S. Pat. No. 4,235,871) for preparing oligolamellar liposomes. ULVs can be produced from MLVs by such methods as sonication (see Papahadjopoulos et al., Biochem. Biophys. Acta, 135, 624 (1968)) or extrusion (U.S. Pat. No. 5,008,050 and U.S. Pat. No. 5,059,421). The liposome of this invention can be produced by the methods of any of these disclosures, the contents of which are incorporated herein by reference.

Various methodologies, such as sonication, homogenisation, French Press application and milling can be used to prepare liposomes of a smaller size from larger liposomes. Extrusion (see U.S. Pat. No. 5,008,050) can be used to size reduce liposomes, that is to produce liposomes having a predetermined mean size by forcing the liposomes, under pressure, through filter pores of a defined, selected size. Tangential flow filtration (see WO 89/08846), can also be used to regularise the size of liposomes, that is, to produce liposomes having a population of liposomes having less size heterogeneity, and a more homogeneous, defined size distribution. The contents of these documents are incorporated herein by reference. Liposome sizes can also be determined by a number of techniques, such as quasi-electric light scattering, and with equipment, e.g., Nicomp® particle sizers, well within the possession of ordinarily skilled artisans.

It is quite interesting to note that the lipid derivatives of the present invention can constitute the major part of a lipid-based system even if this system is a liposome system. This fact resides in the structural (but not functional) similarity between the lipid derivatives of the present invention and lipids. Thus, it is believed that the lipid derivatives for the present invention can be the sole constituent of liposomes, i.e. up to 100 mol % of the total dehydrated liposomes can be constituted by the lipid derivatives. This is in contrast to the known mono-ether lysolipids, which can only constitute a minor part of the liposomes.

Typically, as will be described in detail below, liposomes advantageously include other constituents which may or may not have a pharmaceutical effect, but which will render the liposome structure more stable (or alternatively more unstable) or will protect the liposomes against clearance and will thereby increase the circulation time thereby improving the overall efficiency of a pharmaceutical including the liposome.

This being said, it is believed that the particular lipid derivatives will typically constitute from 15-100 mol %, such as 50-100 mol %, preferably from 75-100 mol %, in particular 90-100 mol %, based on the total dehydrated liposome.

The liposomes can be unilamellar or multilamellar. Some preferred liposomes are unilamellar and have diameters of less than about 200 nm, more preferably, from greater than about 50 nm to less than about 200 nm.

The liposomes are typically—as known in the art—prepared by a method comprising the steps of: (a) dissolving the lipid derivative in an organic solvent; (b) removing the organic solvent from the lipid derivative solution of step (a); and (c) hydrating the product of step (b) with an aqueous solvent so as to form liposomes.

The method further comprises a step of adding a label to the organic solvent of step (a) or the aqueous phase of step (c). Alternatively, ionisable labels can be loaded into liposomes by first forming the liposomes, establishing an electrochemical potential, e.g., by way of a pH gradient, across the outermost liposomal bilayer, and then adding the ionisable label to the aqueous medium external to the liposome (see, e.g., U.S. Pat. No. 5,077,056 and WO 86/01102).

Subsequently, the method may comprise a step of extruding the liposomes produced in step (c) through a filter to produce liposomes of a certain size, e.g. 100 nm.

Lipid-based particulate systems, i.e. liposomes as well as micelles; of sizes covering a broad range may be prepared according to the above-mentioned techniques. Depending on the route of administration, suitable sizes for pharmaceutical applications will normally be in the range of 20-10,000 nm, in particular in the range of 30-1000 nm. Sizes in the range of 50-200 nm are normally preferred because liposomes in this size range are generally believed to circulate longer in the vascular system of mammals than do larger liposomes which are more quickly recognised by the mammals' reticuloendothelial systems ("RES"), and hence, more quickly cleared from the circulation. Longer vascular circulation enhances the chance for the lipid-bases system to reach the intended site, e.g., tumours or inflammations.

It is believed that for an image enhancing system as defined in the embodiments herein, which is adapted to be administered via intraveneous and intramuscular injection, the liposomes should preferably have a mean particle size of about 100 nm. Thus, the particle size should generally be in the range of 50-200 nm.

Furthermore, for an image enhancing system adapted to be administered via subcutaneous injection, the liposomes should preferably have a mean particle size from 100 to 5000 nm, and the liposomes can then be uni- or multilayered.

One of the advantages by including the lipid derivatives in liposomes is that the liposome structure, in particular when stabilised as described in the following, will have a much longer vascular circulation time than the lipid derivatives and label as discrete compounds. Furthermore, the lipid derivatives and the label will become more or less inert or even "invisible" when "packed" in liposomes in which lipopolymers or glycolipids are included. This also means than any potential disadvantageous effect, e.g. hemolytic effect, can be suppressed.

The liposomes should preferably act as inert constituents until they react in the area of interest, e.g. cancerous, infected or inflammatorily diseased areas or tissue. As will be described in the following, liposomes may include a number of other constituents. In particular, an image enhancing system according to the invention may further contain a component which controls the release of the label, extracellular $PLA_2$ activity controlling agents or permeability enhancer, e.g. short chain lipids and lipopolymers/glycolipids.

Two very important groups of compounds to be included in liposomes as modifiers are the stabilising compound lipopolymers and glycolipids, such as lipopolymers (e.g. polyethyleneoxide-dipalmitoylphosphatidyl ethanolamine, DPPE-PEG, polyethyleneoxide-distearoylphosphatidylethanolamine, DSPE-PEG) with PEG molecular weight from 100 to 10000 Daltons. It has been shown that lipopolymers function as stabilisers for the liposome, i.e. lipopolymer increases the circulation time, and—which is highly interesting in the present context, as activators for extracellular $PLA_2$. The stabilising effect will be described in the following.

Liposome outer surfaces are believed to become coated with serum proteins, such as opsonins, in mammals' circulatory systems. Without intending in any way to be limited by any particular theory, it is believed that liposome clearance can be inhibited by modifying the outer surface of liposomes such that binding of serum proteins thereto is generally inhibited. Effective surface modification, that is, alterations to the outer surfaces of liposomes which result in inhibition of opsonisation and RES uptake, is believed to be accomplished by incorporating into liposomal bilayers lipids whose polar headgroups have been derivatised by attachment thereto of a chemical moiety which can inhibit the binding of serum proteins to liposomes such that the pharmacokinetic behaviour of the liposomes in the circulatory systems of mammals is altered and the activity of extracellular $PLA_2$ is enhanced as described for the lipopolymers above.

Liposome preparations have been devised which avoid rapid RES uptake and which thus have an increased half-life in the bloodstream. STEALTH® liposomes (Liposome Technology Inc., Menlo Park, Calif.) include polyethyleneglycol (PEG)-grafted lipids at about 5 mol % of the total dehydrated liposome . The presence of polymers on the exterior liposome surface decreases the uptake of liposomes by the organs of the RES. The liposome membranes can be constructed so as to resist the disruptive effects of the surfactant contained therein. For example, a liposome membrane which contains as constituents lipids derivatised with a hydrophilic (i.e., water-soluble) polymer normally has increased stability. The polymer component of the lipid bilayer protects the liposome from uptake by the RES, and thus the circulation time of the liposomes in the bloodstream is extended.

Hydrophilic polymers suitable for use in lipopolymers are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight from about 100 or 120 daltons up to about 5,000 or 10,000 daltons, and more preferably from about 300 daltons to about 5,000 daltons. In a particularly preferred embodiment, the polymer is polyethyleneglycol having a molecular weight from about 100 to about 5,000 daltons, and more preferably having a molecular weight from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilises polymers of at least about three monomers, such PEG polymers consisting of three monomers (approximately 150 daltons). Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatised celluloses such as hydroxymethylcellulose or hydroxyethylcellulose.

Glycolipids are lipids to which a hydrophilic polysaccharide chain is covalently attached. It will be appreciated that glycolipids can be utilised like lipopolymers although the lipopolymers currently presents the most promising results.

It is generally believed that the content of lipopolymer advantageously will be in the range of 1-50 mol %, such as 2-25%, in particular 2-15 mol %, based on the total dehydrated liposome.

The liposomes' bi- or multilayers may also contain other constituents such as other lipids, sterolic compounds, polymer-ceramides as stabilisers and targeting compounds, etc.

The liposomes comprising lipid derivatives may (in principle) exclusively consist of the lipid derivatives. However, in order to modify the liposomes, "other lipids" may be included as well. Other lipids are selected for their ability to adapt compatible packing conformations with the lipid derivative components of the bilayer such that all the lipid constituents are tightly packed, and release of the lipid derivatives from the bilayer is inhibited. Lipid-based factors contributing to compatible packing conformations are well known to ordinarily skilled artisans and include, without limitation, acyl chain length and degree of unsaturation, as well as the headgroup size and charge. Accordingly, suitable other lipids, including various phosphatidylethanolamines ("PE's") such as egg phosphatidylethanolamine ("EPE") or dioleoyl phosphatidylethanolamine ("DOPE"), can be selected by ordinarily skilled artisans without undue experimentation. Lipids may be modified in various way, e.g. by headgroup derivatisation with dicarboxylic acids, such as glutaric, sebacic, succinic and tartaric acids, preferably the dicarboxylic acid is glutaric acid ("GA"). Accordingly, suitable headgroup-derivatised lipids include phosphatidylethanolamine-dicarboxylic acids such as dipalmitoyl phosphatidylethanolamine-glutaric acid ("DPPE-GA"), palmitoyloleoyl phosphatidylethanolamine-glutaric acid ("POPE-GA") and dioleoyl phosphatidylethanolamine-glutaric acid ("DOPE-GA"). Most preferably, the derivatised lipid is DOPE-GA.

The total content of "other lipids" will typically be in the range of 0-30 mol %, in particular 1-10 mol %, based on the total dehydrated liposome.

Sterolic compound included in the liposome may generally affects the fluidity of lipid bilayers. Accordingly, sterol interactions with surrounding hydrocarbon groups generally inhibit emigration of these groups from the bilayer. An example of a sterolic compound (sterol) to be included in the liposome is cholesterol, but a variety of other sterolic compounds are possible. It is generally believed that the content of sterolic compound, if present, will be in the range of 0-25 mol %, in particular 0-10 mol %, such as 0-5 mol %, based on the total dehydrated liposome.

Polymer-ceramides are stabilisers improving the vascular circulation time. Examples are polyethylene glycol derivatives of ceramides (PEG-ceramides), in particular those where the molecular weight of the polyethylene glycol is from 100 to 5000. It is generally believed that the content of polymer-ceramides, will be in the range of 0-30 mol %, in particular 0-10 mol %, based on the total dehydrated liposome.

Still other ingredients may constitute 0-2 mol %, in particular 0-1 mol %, based on the total dehydrated liposome.

Figure 10:
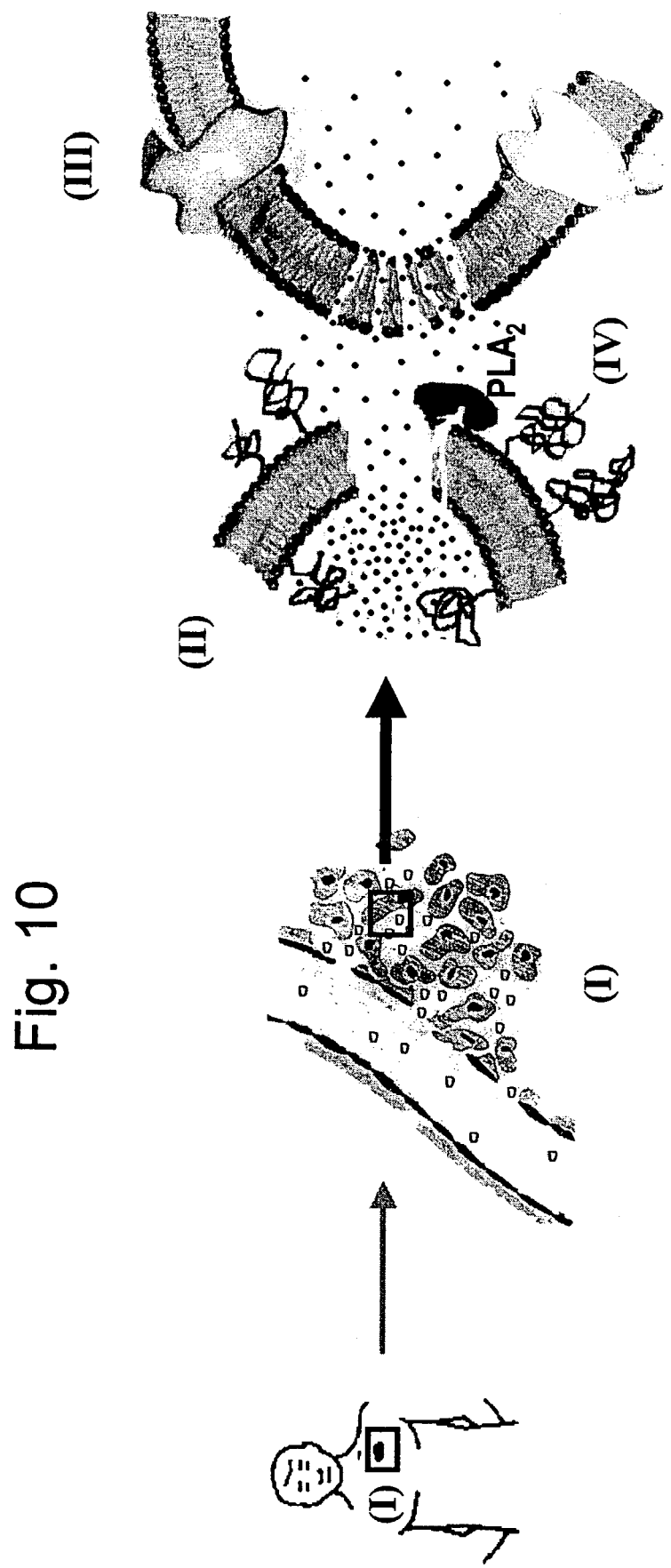
FIG. 10. Describes the principle of liposomal drug and/or contrast agent targeting, release and absorption by extracellular enzymes.

According to an embodiment of the present invention, the lipid bilayer of a liposome contains lipids derivatised with polyethylene glycol (PEG), such that the PEG chains extend from the inner surface of the lipid bilayer into the interior space encapsulated by the liposome, and extend from the exterior of the lipid bilayer into the surrounding environment (see e.g. U.S. Pat. No. 5,882,679 and FIGS. 10 and 11).

A variety of coupling methods for preparing a vesicle-forming lipid derivatised with a biocompatible, hydrophilic polymer such as polyethylene glycol are known in the art (see, e.g., U.S. Pat. No. 5,213,804; U.S. Pat. No. 5,013,556).

The derivatised lipid components of liposomes according to the present invention may additionally include a labile lipid-polymer linkage, such as a peptide, ester, or disulfide linkage, which can be cleaved under selective physiological conditions, such as in the presence of peptidase or esterase enzymes or reducing agents. Use of such linkages to couple polymers to phospholipids allows the attainment of high blood levels of such liposomes for several hours after administration, followed by cleavage of the reversible linkages and removal of the polymer from the exterior liposome bilayer. The polymer-less liposomes are then subject to rapid uptake by the RES system (see, e.g., U.S. Pat. No. 5,356,633).

Additionally, liposomes according to the present invention may contain non-polymer molecules bound to the exterior of the liposome, such as haptens, enzymes, antibodies or antibody fragments, cytokines and hormones (see, e.g., U.S. Pat. No. 5,527,528), and other small proteins, polypeptides, single sugar polysaccharide moieties, or non-protein molecules which confer a particular enzymatic or surface recognition feature to the liposome. See published PCT application WO 94/21235. Surface molecules which preferentially target the liposome to specific organs or cell types are referred to herein as "targeting molecules" and include, for example, antibodies and sugar moieties, e.g. gangliosides or those based on mannose and galactose, which target the liposome to specific cells bearing specific antigens (receptors for sugar moieties). Techniques for coupling surface molecules to liposomes are known in the art (see, e.g., U.S. Pat. No. 4,762,915).

The liposome can be dehydrated, stored and then reconstituted such that a substantial portion of its internal contents is retained. Liposomal dehydration generally requires use of a hydrophilic drying protectant such as a disaccharide sugar at both the inside and outside surfaces of the liposome bilayers (see U.S. Pat. No. 4,880,635). This hydrophilic compound is generally believed to prevent the rearrangement of the lipids in the liposome, so that the size and contents are maintained during the drying procedure and through subsequent rehydration. Appropriate qualities for such drying protectants are that they are strong hydrogen bond acceptors, and possess stereochemical features that preserve the intramolecular spacing of the liposome bilayer components. Alternatively, the drying protectant can be omitted if the liposome preparation is not frozen prior to dehydration, and sufficient water remains in the preparation subsequent to dehydration.

Lipid Derivative Liposomes as Label Carrier Systems

The lipid-based system can be use for diagnosis of a variety of diseases, e.g. typically those selected from cancer, e.g. a brain, breast, lung, colon or ovarian cancer, or a leukemia, lymphoma, sarcoma, carcinoma, and inflammatory conditions.

As mentioned above, the liposomes including the lipid derivatives of the present invention also includes a label. The label may either be covalently linked to the lipid derivative molecules or may—which more often occurs—be incorporated in lipid based system, e.g. in the interior or a micelle of liposome or in the membrane part or a micelle or liposome. In a particular embodiment, the lipid-based image enhancing system described above is in the form of liposomes comprising the label. The lipid based system may in a further embodiment have included therein a second drug substance (pharmaceutically active ingredients) which may have an individual or synergistic pharmaceutical effect in combination with the lipid derivative and lysolipid derivatives whereby the lipid-bases system has a dual effect, namely the targeted delivery of a label as well as a drug or drug mixture.

This being said, the present invention also provides an image enhancing system which is in the form of liposomes, and wherein a second drug substance is incorporated.

A possible "second drug substance" is any compound or composition of matter that can be administered to mammals, preferably humans. Such agents can have biological activity in mammals. Second drug substances which may be associated with liposomes include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; mydriatic compounds; bronchodilators; local anesthetics; and the like. Particularly interesting second drug substances are selected from (i) antitumour agents such as anthracyline derivatives, cisplatin, paclitaxel, 5-fluoruracil, exisulind, cis-retinoic acid, suldinac sulfide and vincristine, (ii) antibiotics and antifungals, and (iii) antiinflammatory agents such as steroids and non-steroids. In particular the steroids can also have a stabilising effect on the liposomes.

The present invention also relates to the use of any of the lipid-based image enhancing systems described herein as a combined diagnostic composition and medicament, and to the use of any of the lipid-based image enhancing systems described herein for the preparation of a medicament for the treatment of diseases or conditions associated with a localised increase in extracellular phospholipase A2 activity in mammalian tissue. Such diseases or conditions are typically selected from cancer, e.g. a brain, breast, lung, colon or ovarian cancer, or a leukemia, lymphoma, sarcoma, carcinoma and inflammatory conditions.

Pharmaceutical Preparations and Diagnostic Uses

Also provided herewith is a pharmaceutical composition comprising a pharmaceutically acceptable carrier, the lipid derivative and a label.

"Pharmaceutically acceptable carriers" as used herein are those media generally acceptable for use in connection with the administration of lipids and liposomes, including liposomal drug formulations, to mammals, including humans.

Pharmaceutically acceptable carriers are generally formulated according to a number of factors well within the purview of the ordinarily skilled artisan to determine and account for, including without limitation: the particular lipid-conjugated contrast agents and/or second drug substance used, the liposome preparation, its concentration, stability and intended bioavailability; the disease, disorder or condition being treated with the liposomal composition; the subject, its age, size and general condition; and the composition's intended route of administration, e.g., nasal, oral, ophthalmic, subcutaneous, intramammary, intraperitoneal, intravenous, or intramuscular. Typical pharmaceutically acceptable carriers used in parenteral drug administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and anti-oxidants.

The liposome or lipid derivative is typically formulated in a dispersion medium, e.g. a pharmaceutically acceptable aqueous medium.

For normal diagnostic applications, an amount of the composition comprising the label, typically from about 0.1 to about 1000 mg of lipid derivative per kg of the mammal's body, is administered, preferably intravenously.

The pharmaceutical composition is preferably administered parenterally by injection, infusion or implantation (intravenous, intramuscular, intraarticular, subcutaneous or the like) in dosage forms, formulations or e.g. suitable delivery devices or implants containing conventional, non-toxic pharmaceutically acceptable carriers and adjuvants.

The formulation and preparation of such compositions is well-known to those skilled in the art of pharmaceutical formulation. Specific formulations can be found in the textbook entitled "Remington's Pharmaceutical Sciences".

Thus, the pharmaceutical compositions according to the invention may comprise the lipid-bases system in the form of a sterile injection. To prepare such a composition, the suitable lipid-conjugated contrast agents s are dispersed in a parenterally acceptable liquid vehicle which conveniently may comprise suspending, solubilising, stabilising, pH-adjusting agents and/or dispersing agents. Among acceptable vehicles that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate.

When diagnosis of a tumour or neoplasm is desired, effective delivery of a liposome-encapsulated label via the bloodstream requires that the liposome be able to penetrate the continuous (but "leaky") endothelial layer and underlying basement membrane surrounding the vessels supplying blood to a tumour. Liposomes of smaller sizes have been found to be more effective at extravasation into tumours through the endothelial cell barrier and underlying basement membrane which separates a capillary from tumour cells.

As used herein, "solid tumours" are those growing in an anatomical site other than the bloodstream (in contrast to blood-borne tumours such as leukemias). Solid tumours require the formation of small blood vessels and capillaries to nourish the growing tumour tissue.

In accordance with the present invention, the label of choice is entrapped within a liposome according to the present invention; the liposomes are formulated to be of a size known to penetrate the endothelial and basement membrane barriers. The resulting liposomal formulation can be administered parentally to a subject in need of such treatment, preferably by intravenous administration. Tumours characterised by an acute increase in permeability of the vasculature in the region of tumour growth are particularly suited for treatment by the present methods. The liposomes will eventually degrade due to lipase action at the tumour site, or can be made permeable by, for example, thermal or ultrasonic radiation. The label is then released in a bioavailable, transportable solubilised form. Even if the label is not released, the mere fact that the liposome is concentrated in the tissue of interest makes the diagnosis feasible. Furthermore, a small elevation in temperature as often seen in diseased tissue may further increase the stimulation of extracellular $PLA_2$.

The disease or condition to be diagnosed are characterised by having an elevated $PLA_2$ level in a mammal is often caused by malignant tissue, e.g. selected from the group consisting of brain cancer, breast cancer, lung cancer, colon cancer, ovarian cancer, lymphoma, sarcoma and carcinoma. The malignant tissue is typically the primary tumour. The malignant tissue is alternatively metastatic cells originating from the primary tumour.

Where site-specific targeting of inflammation is desired, effective liposome delivery of a label requires that the liposome have a long blood half-life, and be capable of penetrating the continuous endothelial cell layer and underlying basement membrane surrounding blood vessels adjacent to the site of inflammation. Liposomes of smaller sizes have been found to be more effective at extravasation through the endothelial cell barrier and into associated inflamed regions. However, the limited label-carrying capacity of conventional small liposome preparations has limited their effectiveness for such purposes.

In accordance with the present invention, the label of choice is entrapped within a liposome according to the present invention; the liposomes are formulated to be of a size known to penetrate the endothelial and basement membrane barriers. The resulting liposomal formulation can be administered parenterally to a subject to be diagnosed, preferably by intravenous administration. Inflamed regions characterised by an acute increase in permeability of the vasculature in the region of inflammation are particularly suited for targeting by the present methods.

It is known that the activity of extracellular $PLA_2$ is abnormally high in areas of the mammalian body diseased by cancer, inflammation, etc. The present invention have provided a way of exploiting this fact, and it is believed that the extracellular $PLA_2$ activity should be at least 25% higher in the diseases area of the body (determined in the extracellular environment) compared with a comparative normal area. It is however envisaged that the level of extracellular $PLA_2$ activity often is much higher, e.g. at least 100%, e.g. at least 200% such as at least 400%. This means that diagnosis of a mammal, can be conducted with only minimal influence on tissue having a "normal" level of extracellular $PLA_2$ activity.

The label can be adapted so as to be detectable and optionally quantifiable by a detection method selected from the group consisting of positron emission tomography (PET), X-ray, gamma-scintigraphy, magnetic resonance (MR) imaging, computed tomography (CT) imaging and ultrasonography.

The invention will be illustrated by the following non-limiting examples.

EXAMPLES

The examples illustrates the preparation and test of liposomal preparations. Preparation of compositions for diagnostic use can be prepared as described herein.

Example 1

Liposome Preparation

Unilamellar fully hydrated liposomes with a narrow size distribution were made from 1-O-hexadecyl-2-hexadecanoyl-sn-glycero-3-phosphocholine (1-O-DPPC) and di-hexa-decanoyl-sn-glycero-3-phosphocholine (DPPC). DPPC were obtained from Avanti Polar lipids and 1-O-DPPC were synthesised in our laboratory. Briefly, weighed amounts of DPPC or 1-O-DPPC were dissolved in chloroform. The solvent was removed by a gentle stream of $N_2$ and the lipid films were dried overnight under low pressure to remove trace amounts of solvent. Multilamellar vesicles were made by dispersing the dried lipids in a buffer solution containing: 150 mM KCL, 10 mM HEPES (pH=7.5), 1 mM $NaN_3$, 30 µM $CaCl_2$ and 10 µM EDTA. The multilamellar vesicles were extruded ten times through two stacked 100 nm pore size polycarbonate filters as described by Mayer et al., *Biochim. Biophys. Acta*, 858, 161-168.

Heat capacity curves were obtained using a N-DSC II differential scanning calorimeter (Calorimetry Sciences Corp., Provo) of the power compensating type with a cell volume of 0.34 mL. Before scanning, the liposome suspension was equilibrated for 50 min in the calorimeter at the starting temperature. A scan rate of +10° C./h was used. The lipid concentration was 1 mM. The gel-to-fluid transition of the multilamellar liposomes (MLV) is characterised as a sharp first-order transition, as reflected by the narrow peak in the heat capacity curves shown in FIGS. 1a and 1b (upper curves) for 1-O-DPPC and DPPC. The sharp peak reflects the transitional behaviour of multilamellar liposomes and is in contrast to the broader gel-to-fluid transition observed for unilamellar liposomes (LUV) (Pedersen et al., 1996, *Biophys. J.* 71, 554-560) as shown in FIGS. 1a and 1b (lower curves) for the unilamellar extruded 1-O-DPPC and DPPC liposomes.

Example 2

Phospholipase $A_2$ Reaction Profile and Lag Time Measurements

Purified snake-venom phospholipase $A_2$ (PLA$_2$ from *Agikistrodon piscivorus piscivorus*) has been isolated according to the procedure of Maraganore et al., *J. Biol. Chem.* 259, 13839-13843. This PLA$_2$ enzyme belongs to the class of low-molecular weight 14 kD secretory enzymes which display structural similarity to human extracellular phospholipase $A_2$ indicating a common molecular mechanisms of the phospholipase catalysed hydrolysis at the lipid-membrane interface (Wery et al., *Nature* 352, 79-82; Hønger et al. *Biochemistry* 35, 9003-9006; Vermehren et al., *Biochimica et Biophysica Acta* 1373, 27-36). Unilamellar fully hydrated liposomes with a narrow size distribution were prepared from 1-O-hexadecyl-2-hexadecanoyl-sn-glycero-3-phosphocholine (1-O-DPPC) and from 1-O-DPPC with 5 and 10 mol % 1-O-hexadecyl-2-hexadecanoyl-sn-glycero-3-phosphoethanolamine-N-[methoxy (polyethylene glycol)-350] (1-O-DPPE-PEG350) or 5 and 10 mol % 1-O-hexadecyl-2-hexadecanoyl-sn-glycero-3-phosphoethanolamine-N-[methoxy(polyethylene glycol)-2000] (1-O-DPPE-PEG2000) as described above. Assay conditions for the PLA$_2$ reaction time profile shown in FIG. 2 and the lag-time and percent hydrolysis reported in Table 1 were: 0.15 mM unilamellar liposomes, 150 nM PLA$_2$, 150 mM KCL, 10 mM HEPES (pH 7.5), 1 mM $NaN_3$, 30 µM $CaCl_2$, and 10 µM EDTA.

TABLE 1

Lag-time and percent hydrolysed 1-O-DPPC at 41° C. as determined by HPLC. The lipid concentration was 0.150 mM in a 10 mM HEPES-buffer (pH = 7.5).

| Composition | Lag-time (sec) | 1-O-DPPC (%) |
|---|---|---|
| 100% 1-O-DPPC | 583 | 79 |
| 95% 1-O-DPPC/5% 1-O-DPPE-PEG350 | 128 | 73 |
| 90% 1-O-DPPC/10% 1-O-DPPE-PEG350 | 26 | 75 |
| 95% 1-O-DPPC/5% 1-O-DPPE-PEG2000 | 450 | 56 |
| 90% 1-O-DPPC/10% 1-O-DPPE-PEG2000 | 20 | 89 |

Figure 2:
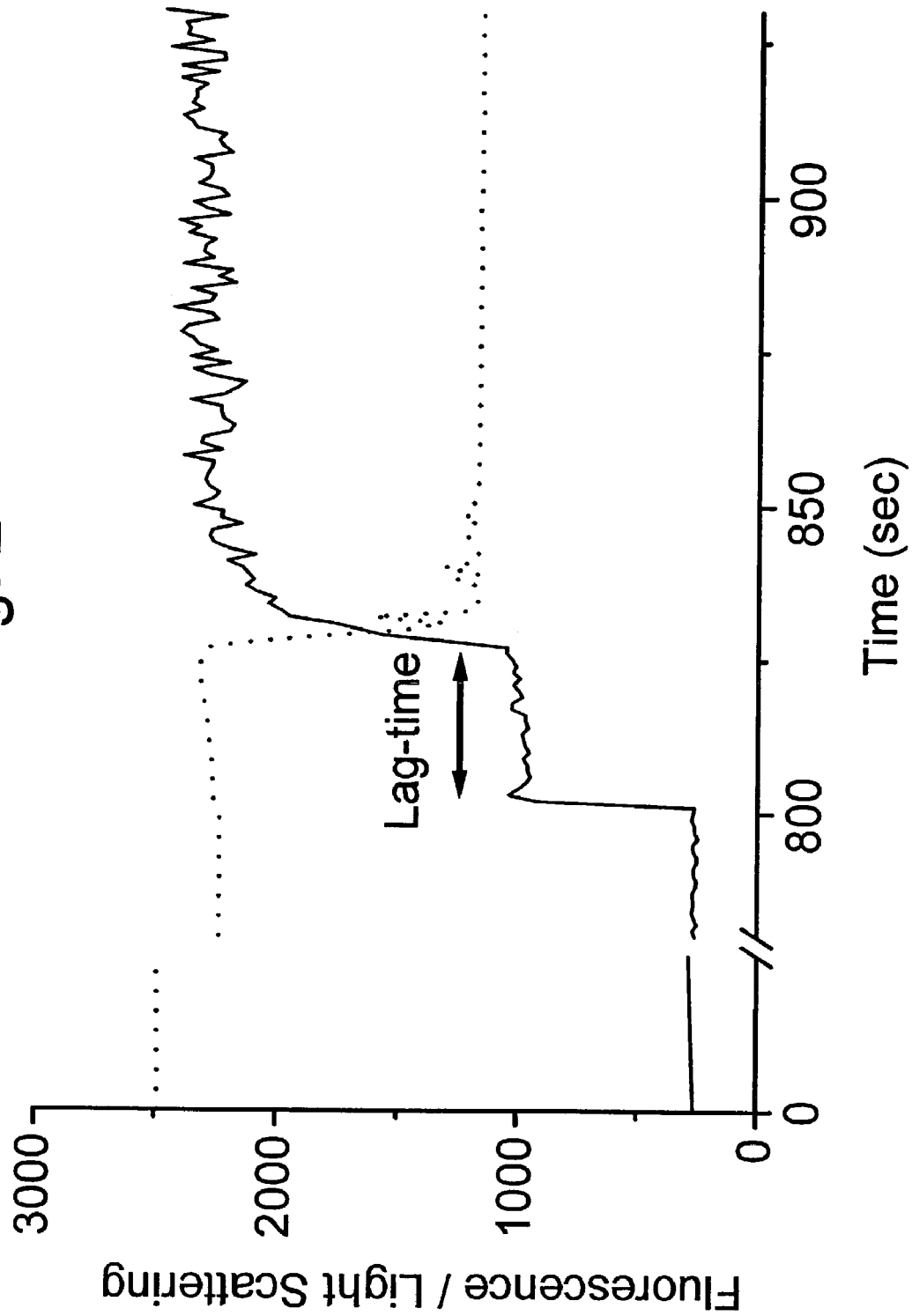
FIG. 2. Characteristic reaction time profile at 41° C. for phospholipase A$_2$, PLA$_2$, (*A. piscivorus piscivorus*) hydrolysis of unilamellar 1-O-DPPC-liposomes composed of 90% 1-O-DPPC and 10% 1-O-hexadecyl-2-hexadecanoyl-sn-glycero-3-phosphoethanolamine-N-[methoxy(polyethylene glycol)-350] (1-O-DPPE-PEG350). The PLA$_2$ hydrolysis reaction is monitored by intrinsic fluorescence (solid line) from the enzyme and 90° static light scattering (dashed lines) from the lipid suspension. After adding PLA$_2$, at 800 sec to the equilibrated liposome suspension a characteristic lag-time follows before a sudden increase in the catalytic activity takes place. Samples for HPLC were taken before adding the enzyme and 20 minutes after the observed lag time.
Figure 3:
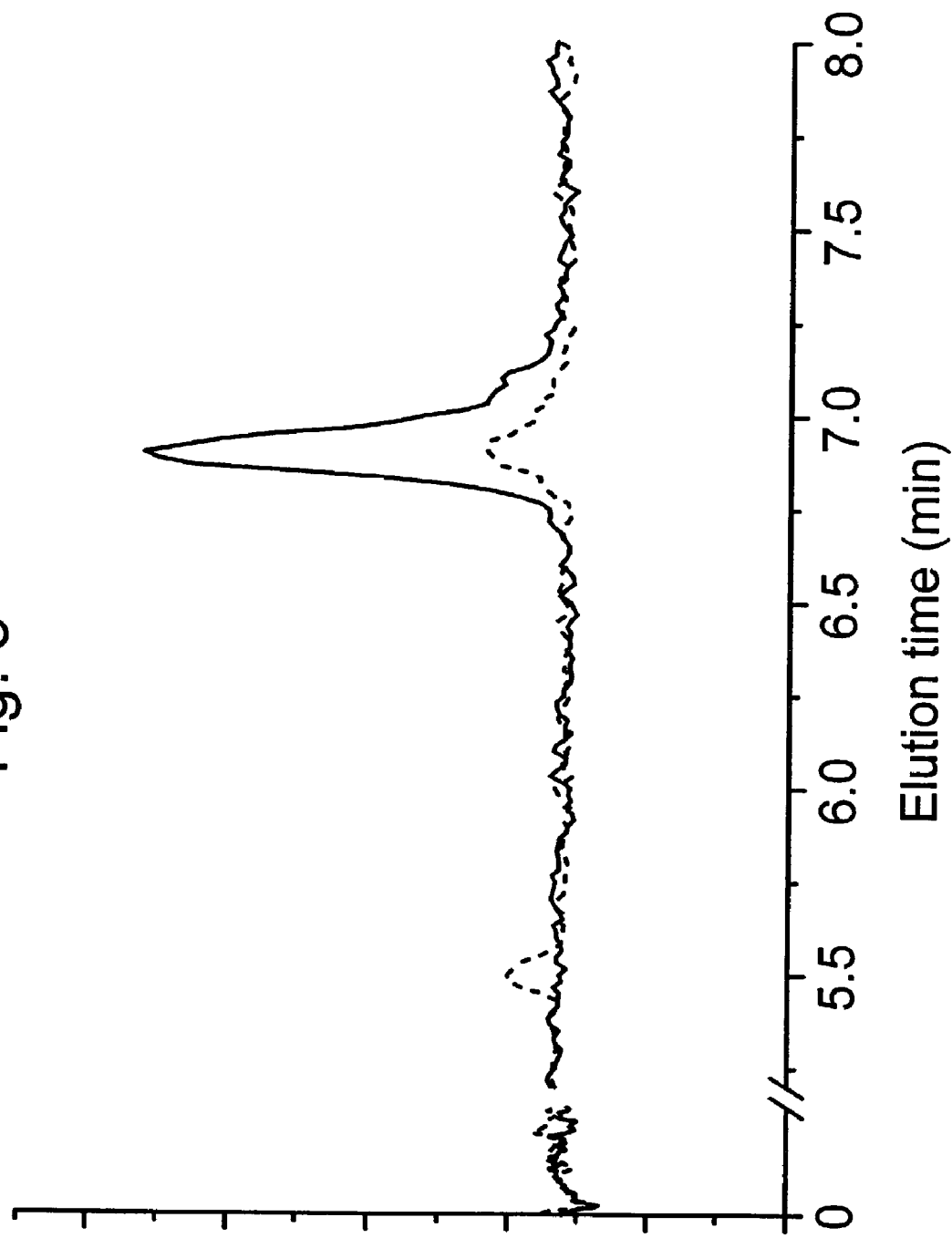
FIG. 3. HPLC chromatograms illustrating the effect of phospholipase A$_2$ hydrolysis of liposomes composed of 90% 1-O-DPPC and 10% 1-O-DPPE-PEG350. The chromatograms show the amount of 1-O-DPPC (100%, solid line) before phospholipase A$_2$ (*A. piscivorus piscivorus*) was added to the liposome suspension and the amount of 1-O-DPPC (75%, dashed line) after the lag-burst.

The catalytic reaction was initiated by adding 8.9 µL of a 42 µM PLA$_2$ (150 nM) stock solution to 2.5 ml of the thermostated liposome suspension (0.150 mM) equilibrated for 800 sec prior to addition of PLA$_2$. The characteristic lag-burst behaviour of PLA$_2$ towards the liposomes is signalled by a sudden increase in the intrinsic fluorescence from PLA$_2$ at 340 nm after excitation at 285 nm followed by a concomitant decrease in the 900 light scattering from the lipid suspension (Hønger et al., *Biochemistry* 35, 9003-9006). Samples for HPLC analysis of the amount of non-hydrolysed 1-O-DPPC remaining and consequently the amount of 1-O-hexadecyl-2-hydroxy-sn-glycero-3-phosphocholine (lyso-1-O-PPC) generated were taken before adding PLA$_2$ and 1200 sec after the observed lag-time. 100 µl aliquots were withdrawn from the lipid suspension and rapidly mixed with 1 ml chloroform/methanol/acetic acid (2:4:1) solution in order to quench the enzymatic reaction. The solution was washed with 1 ml of water and 20 µl of the heavy organic phase was used for HPLC. The HPLC chromatograms in FIG. 3 show the amounts of 1-O-DPPC before and after (t=2050 sec) the addition of PLA$_2$ (t=800 sec) to the liposome suspension. HPLC analysis was made using a 5 µm diol column, a mobile phase composed of chloroform/methanol/water (730:230:30, v/v) and an evaporative light scattering detector. The turnover of the PLA$_2$ catalysed lipid hydrolysis of 1-O-DPPC to lyso-1-O-PPC was measured by HPLC (see Table 1). The intrinsic enzyme fluorescence and 90° light scattering were measured as a function of time as shown in FIG. 2.

Example 3

Phospholipase A$_2$ Induced Release of an Incapsulated Water-Soluble Model Drug and/or Contrast Agent Multilamellar 1-O-DPPC-liposomes were made in the presence of fluorescent calcein in a self-quenching concentration of 20 mM by hydrating a film of 1-O-hexadecyl-2-hexadecanoyl-sn-glycero-3-phosphocholine in a HEPES buffer solution at pH=7.5 for one hour at 10° C. above the phase transition temperature. Unilamellar liposomes were formed by extruding the multilamellar liposomes ten times through two stacked 100 nm polycarbonate filters. The unilamellar liposomes were rapidly cooled to a temperature below the transition temperature, and the calcein-containing 1-O-DPPC liposomes were separated from free calcein using a chromatographic column packed with Sephadex G-50.

Figure 4:
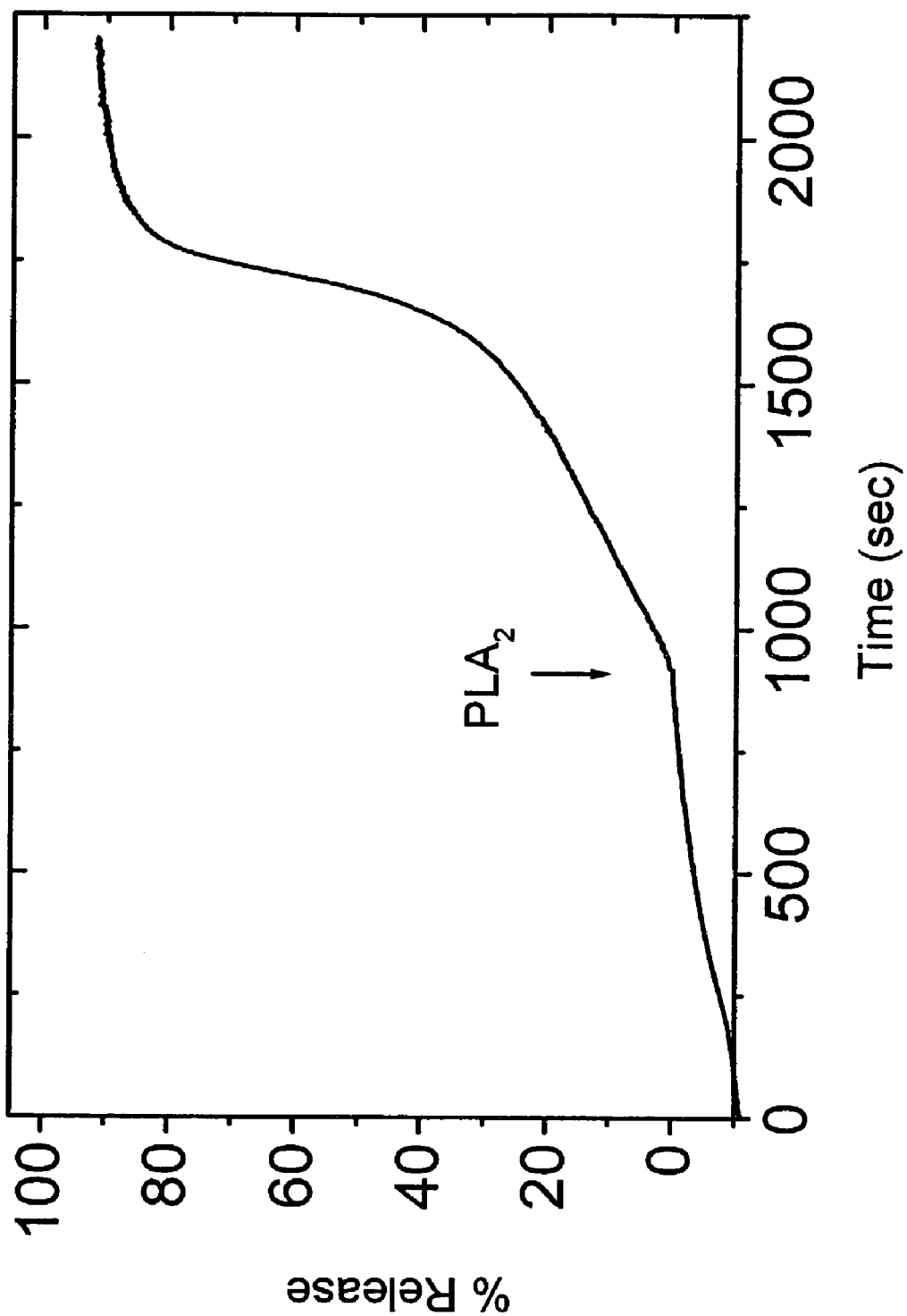
FIG. 4. PLA$_2$-controlled release of the fluorescent model drug and/or contrast agent calcein from liposomes composed of 25 µM 1-O-hexadecyl-2-hexadecanoyl-sn-glycero-3-phosphocholine (1-O-DPPC) suspended in a 10 mM HEPES-buffer (pH=7.5), as a function of time. 25 nM phospholipase A$_2$ (*A. piscivorus piscivorus*) was added at time 900 sec, the temperature was 37° C. The percentage of calcein released is determined as % Release=100($I_{F(t)}$−$I_B$)/($I_T$−$I_B$), where $I_{F(t)}$ is the measured fluorescence at time t after addition of the enzyme, $I_B$ is the background fluorescence, and $I_T$ is the total fluorescence measured after addition of Triton X-100 which leads to complete release of calcein by breaking up the liposomes.

Assay conditions for the $PLA_2$ induced calcein release were 25 µM unilamellar 1-O-DPPC-liposomes, 25 nM $PLA_2$, 150 mM KCL, 10 mM HEPES (pH 7.5 or 8.0), 1 mM $NaN_3$, 30 µM $CaCl_2$, and 10 µM EDTA. $PLA_2$ was added at time 900 sec to 2.5 ml of the thermostated 1-O-DPPC-liposome suspension equilibrated for at least 20 min at 37° C. prior to addition of $PLA_2$. The percentage of calcein released is determined as: % Release=$100 \times (I_{F(t)} - I_B)/(I_T - I_B)$, where $I_{F(t)}$ is the measured fluorescence at time t after addition of the enzyme, $I_B$ is the background fluorescence, and $I_T$ is the total fluorescence measured after addition of Triton X-100 which leads to complete release of calcein by breaking up the 1-O-DPPC-liposomes. $PLA_2$ induced at total release of 90 percent of the entrapped calcein in the 1-O-DPPC-liposomes as shown in FIG. 4.

Example 4

Phospholipase $A_2$ Controlled Permeability Increase of a Target Model Membrane

Multilamellar model membrane target liposomes were made in the presence of fluorescent calcein in a self-quenching concentration of 20 mM by hydrating a film of 1,2-O-dioctadecyl-sn-glycero-3-phosphatidylcholines (D-O-SPC) in a HEPES buffer solution at pH=7.5 for one hour at 10° C. above the phase transition temperature ($T_m$=55° C.). Unilamellar liposomes were made by extruding the multilamellar target liposomes ten times through two stacked 100 nm polycarbonate filters. The unilamellar liposomes were rapidly cooled to a temperature below the transition temperature, and the calcein-containing liposomes were separated from free calcein using a chromatographic column packed with Sephadex G-50. The unilamellar carrier liposomes composed of 1-O-hexadecyl-2-hexadecanoyl-sn-glycero-3-phosphocholine were prepared as described above. Calcein release from the target liposomes is determined by measuring the fluorescent intensity at 520 nm after excitation at 492 nm.

Figure 5:
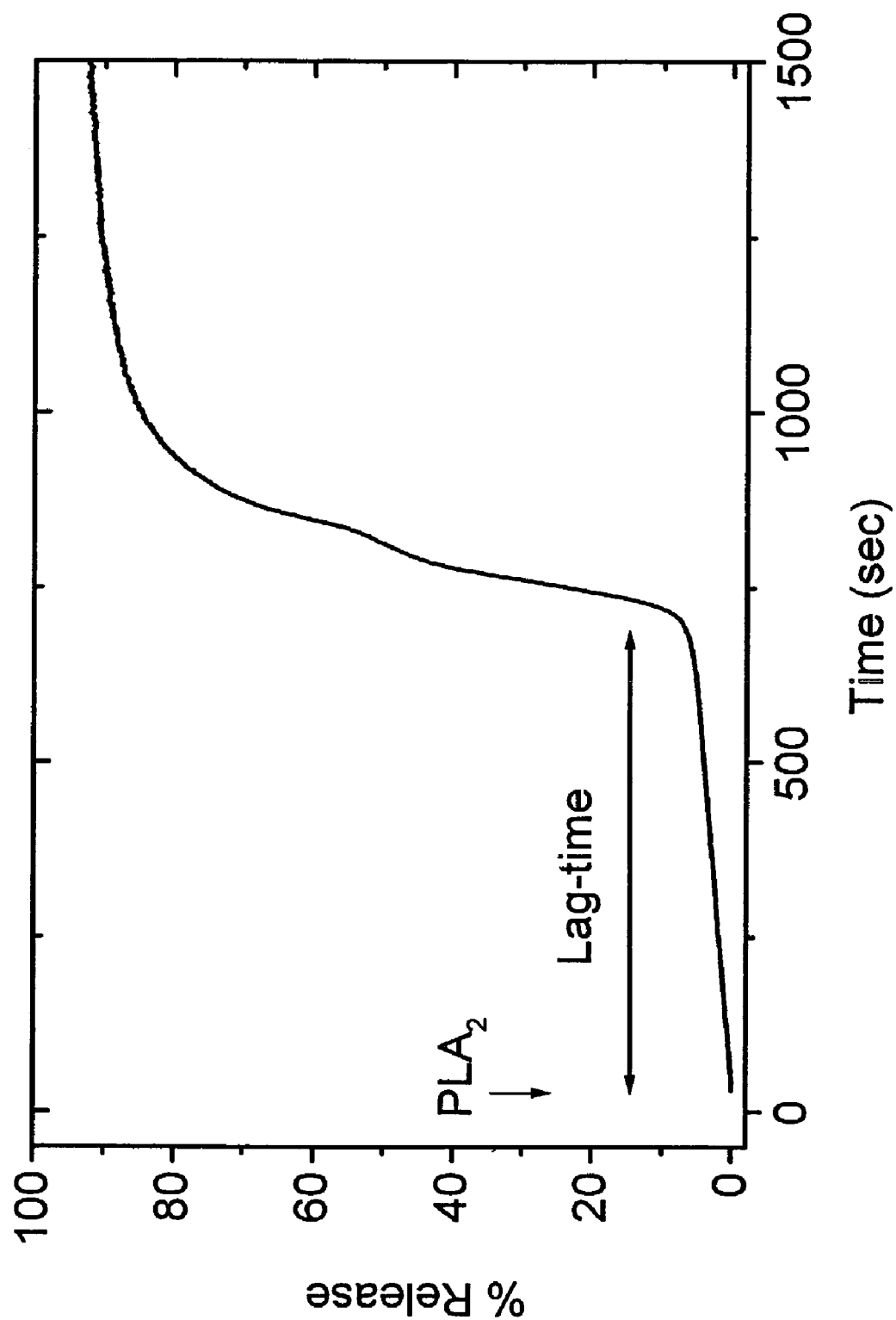
FIG. 5. PLA$_2$-controlled release of the fluorescent calcein across the target membrane of non-hydrolysable membranes (see FIG. 11b), as a function of time for liposomes composed of 25 µM 1-O-hexadecyl-2-hexadecanoyl-sn-glycero-3-phosphocholine (1-O-DPPC) suspended in a 10 mM HEPES-buffer (pH=7.5). 25 nM phospholipase A$_2$ was added at time 0 sec and the temperature was 37° C. The percentage of calcein released is determined as described in FIG. 4.

The concentrations of D-O-SPC and 1-O-DPPC-liposomes were 25 µM. Snake venom $PLA_2$ (*Agkistrodon piscivorus piscivorus*) was added (25 nM) to initiate the hydrolytic reaction leading to the formation of 1-O-hexadecyl-2-hydroxy-sn-glycero-3-phosphocholine (lyso-1-O-PPC) and fatty acid hydrolysis products. As calcein is released from the D-O-SPC liposomes, due to the incorporation of the non-bilayer forming lyso-1-O-PPC and fatty acid hydrolysis products into the target lipid membrane, a linear increase in the fluorescence at 520 nm after excitation at 492 nm is observed when calcein is diluted into the surrounding buffer medium as shown in FIG. 5. The percentage of the model drug and/or contrast agent calcein released is determined as described above (see Example 3).

Example 5

Hemolysis Assay

Unilamellar fully hydrated liposomes with a narrow size distribution were prepared from 1-O-hexadecyl-2-hexadecanoyl -sn-glycero-3-phosphocholine (1-O-DPPC), and from 1-O-DPPC with 5 mol % 1-O-hexadecyl-2-hexadecanoyl-sn-glycero-3-phosphoethanolamine-N-[methoxy (polyethylene glycol)-350] (1-O-DPPE-PEG350) or with 5 mol % 1-O-hexadecyl-2-hexadecanoyl-sn-glycero-3-phosphoethanolamine-N-[methoxy(polyethylene glycol)-2000 (1-O-DPPE-PEG2000). The lipids were hydrated in phosphate buffered saline (PBS). 1-O-octadecyl-2-O-methyl-sn-glycero-3-phosphocholine (ET-18-$OCH_3$) in PBS was included in the assay as a reference.

Figure 6:
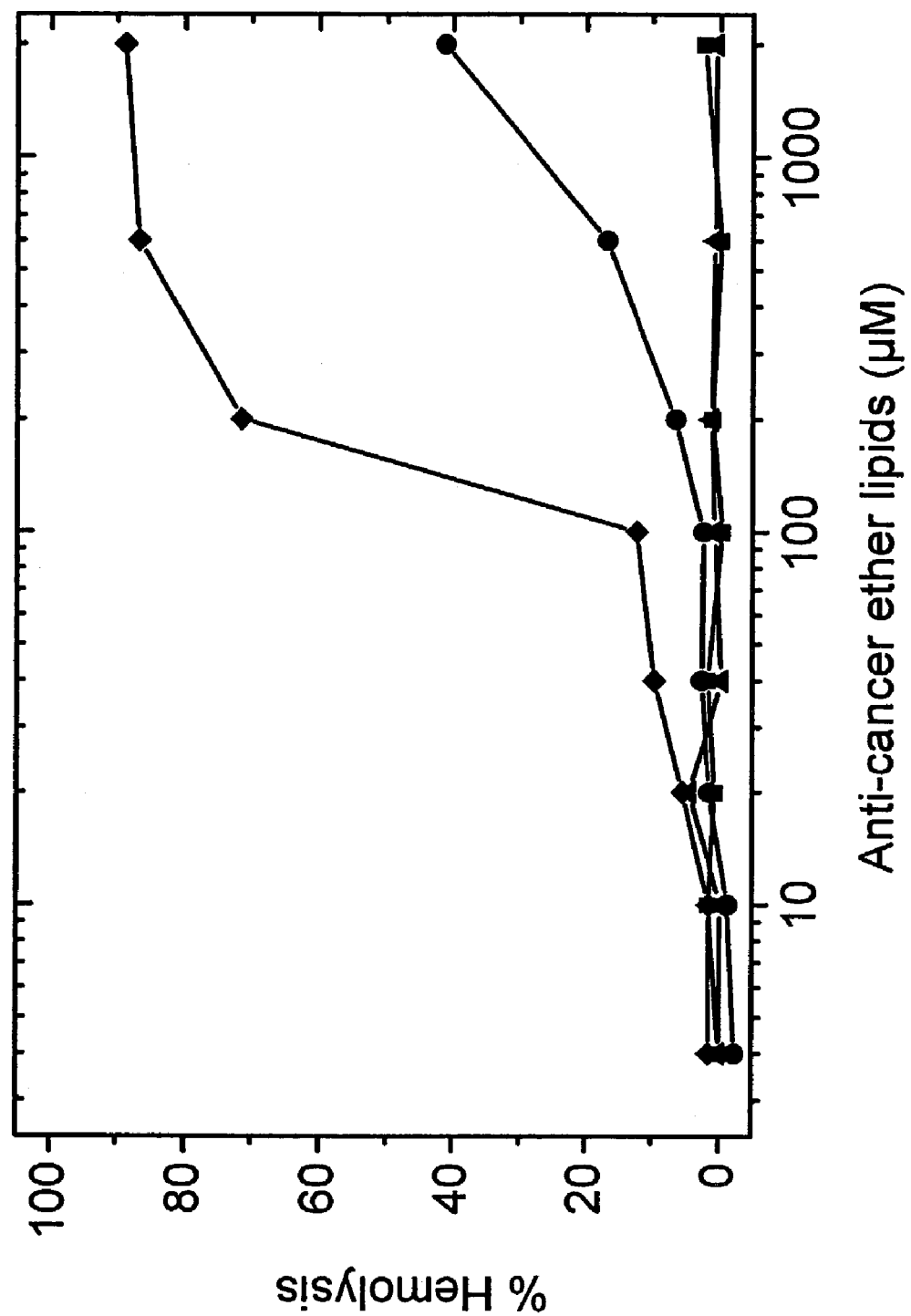
FIG. 6. Hemolysis profile of normal red blood cells in the presence of liposomes composed of 100% 1-O-DPPC (squares); 90% 1-O-DPPC and 10% 1-O-DPPE-PEG350 (triangles); 90% 1-O-DPPC and 10% 1-O-DPPE-PEG2000 (circles) and ET-18-OCH$_3$ (diamonds). The concentrations that yield 5% hemolysis ($H_5$) were well above 2 mM for liposomes composed of 100% 1-O-DPPC, and for liposomes composed of 90%1-O-DPPC with 10% DPPE-PEG350. Hemolysis assay was performed as described by Perkins et al., 1997, Biochimica et Biophysica Acta 1327, 61-68. Briefly, each sample was serially diluted with phosphate buffered saline (PBS), and 0.5 ml of each dilute suspension was mixed with 0.5 ml washed human red blood cells (RBC) [4% in PBS (v/v)]. Sample and standard were placed in a 37° C. incubator and agitated for 20 hours. Tubes were centrifuged at low speed (2000×G) for 10 minutes and 200 µl of the supernatant was quantitated by absorbance at 550 nm. 100 percent hemolysis was defined as the maximum amount of hemolysis obtained from the detergent Triton X-100. The hemolysis profile in FIG. 6 shows a low hemolysis value (below 5% percent) for 2 mM 1-O-DPPC-liposomes and for 1-O-DPPC with 10% 1-O-DPPE-PEG350, liposomes.

Hemolysis assay was performed as described by Perkins et al., *Biochim. et Biophys. Acta* 1327, 61-68. Briefly, each sample was serially diluted with PBS, and 0.5 ml of each dilute suspension of 1-O-DPPC liposomes were mixed with 0.5 ml washed human red blood cells (RBC) [4% in PBS (v/v)]. For controls, 0.5 ml of the red blood cell suspension was mixed with either 0.5 ml buffer solution (negative hemolysis control) or 0.5 ml water (positive hemolysis control). Samples and standard were placed in a 37° C. incubator and agitated for 20 hours. Tubes were centrifuged at low speed (2000×G) for 10 minutes to form RBCs pellets. 200 µl of the supernatant was quantitated by absorbance at 550 nm using a Perkin-Elmer 320 scanning spectrophotometer. 100 percent hemolysis was defined as the maximum amount of hemolysis obtained from the detergent Triton X-100. The hemolysis profile in FIG. 6 shows a low hemolysis value (below 5 percent) for 2 mM 1-O-DPPC-liposomes. FIG. 6 also shows that low concentrations of ET-18-$OCH_3$ induces a significant degree of hemolysis.

Example 6

Enhancement of Phospholipase A2 Activity by Polymer Grafted 1-O-DPPC Lipids

Figure 7:
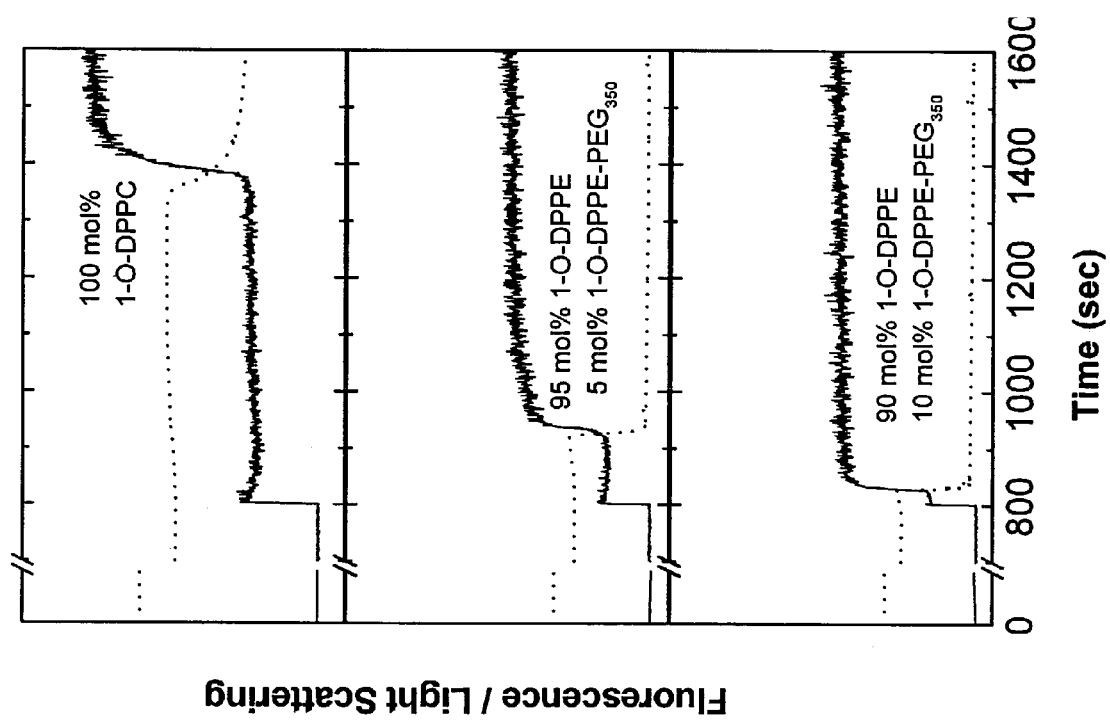
FIG. 7. Characteristic reaction time profiles at 41° C. for PLA$_2$ (*A. piscivorus piscivorus*) hydrolysis of unilamellar liposomes incorporated with 0, 5 and 10% 1-O-DPPE-PEG350 lipopolymers. The PLA$_2$ hydrolysis reaction is monitored by intrinsic fluorescence (solid line) and 90° static light scattering (dashed lines) from the suspension. After adding PLA$_2$ to the equilibrated liposome suspension a characteristic lag-time follows before a sudden increase in the catalytic activity takes place.

Unilamellar fully hydrated liposomes with a narrow size distribution were prepared from 1-O-hexadecyl-2-hexadecanoyl-sn-glycero-3-phosphocholine (1-O-DPPC) and 1-O-DPPC with 5 or 10 mol % 1-O-hexadecyl-2-hexadecanoyl-sn-glycero-3-phosphoethanolamine-N-[methoxy (polyethylene glycol)-350] (1-O-DPPE-PEG350), as described in example 2. Assay conditions for the $PLA_2$ lag-time measurements were 0.15 mM unilamellar liposomes, 150 nM $PLA_2$, 150 mM KCL, 10 mM HEPES (pH 7.5), 1 mM $NaN_3$, 30 µM $CaCl_2$, and 10 µM EDTA. The catalytic reaction was initiated by adding 8.9 µL of a 42 µM $PLA_2$ stock solution to 2.5 ml of the thermostated liposomes suspension equilibrated for 800 seconds at 41° C. prior to addition of $PLA_2$. The time elapsed before the onset of rapid enzymatic activity is determined by a sudden increase in the intrinsic fluorescence from $PLA_2$ at 340 nm after excitation at 285 nm. The results shown in FIG. 7 show a significant decrease in the lag time when 5 and 10 mol % of 1-O-DPPE-$PEG_{350}$ is incorporated into the 1-O-DPPC liposomes.

Example 7

Preparation of Micelles Composed of 1-O-DPPE-PEG350, DSPE-PEG750 and 1-O-DPPE-PEG2000.

Micelles were made from 1-O-hexadecyl-2-hexadecanoyl-sn-glycero-3-phosphoethanol-amine-N-[methoxy (polyethylene glycol)-350] (1-O-DPPE-PEG350), di-octadecanoyl-sn-glycero-3-phosphoethanolamine-N-[methoxy (polyethylene glycol)-750 (DSPE-PEG750) or 1-O-hexadecyl-2-hexadecanoyl-sn-glycero-3-phosphoethanolamine-N-[methoxy(poly-ethylene glycol)-

2000 (1-O-DPPE-PEG2000). Briefly, weighed amounts of the polymer lipids were dissolved in chloroform. The solvent was removed by a gentle stream of $N_2$. The lipid films were then dried overnight under low pressure to remove trace amounts of solvent. Micelles were made by dispersing the dried polymer lipids in a buffer solution containing: 150 mM KCL, 10 mM HEPES (pH=7.5), 1 mM $NaN_3$, 30 µM $CaCl_2$ and 10 µM EDTA.

Example 8

Permeability Increase of a Target Model Membranes Controlled by Phospholipase $A_2$ Hydrolysis of Micelles Multilamellar model membrane target liposomes were made in the presence of fluorescent model drug and/or contrast agent calcein in a self-quenching concentration of 20 mM by hydrating a film of 1,2-O-dioctadecyl-sn-glycero-3-phosphatidylcholines (D-O-SPC) in a HEPES buffer solution at pH=7.5 for one hour at 10° C. above the phase transition temperature ($T_m$=55° C.). Unilamellar liposomes were made by extruding the multilamellar liposomes ten times through two stacked 100 nm polycarbonate filters. The unilamellar liposomes were rapidly cooled to a temperature below the transition temperature, and the calcein-containing liposomes were separated from free calcein using a chromatographic column packed with Sephadex G-50. Micelles composed of 1-O-hexadecyl-2-hexadecanoyl-sn-glycero-3-phosphoethanolamine-N-[methoxy(polyethylene glycol)-350] (1-O-DPPE-PEG350), di-octadecanoyl-sn-glycero-3-phosphoethanolamine-N-[methoxy(polyethylene glycol)-750 (DSPE-PEG750) or 1-O-hexadecyl-2-hexadecanoyl-sn-glycero-3-phosphoethanolamine-N-[methoxy(polyethylene glycol)-2000 (1-O-DPPE-PEG2000) were prepared as described in example 7. Calcein release from the target liposome is determined by measuring the fluorescent intensity at 520 nm after excitation at 492 nm.

Figure 8:
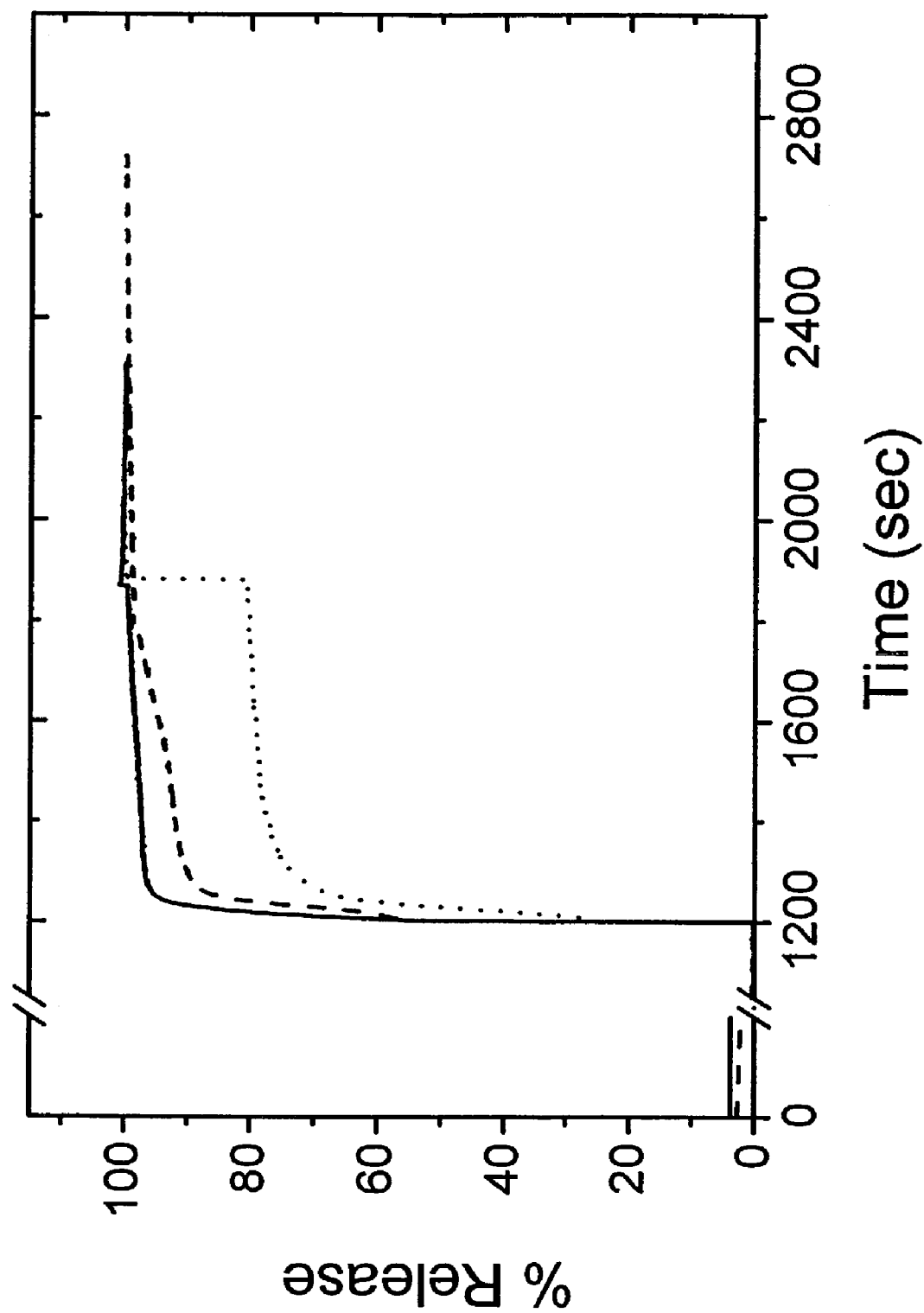
FIG. 8. PLA$_2$-controlled release of the fluorescent model drug and/or contrast agent calcein across the target membrane of non-hydrolysable D-O-SPC-membranes as a function of time for micelles composed of 25 µM 1-O-DPPE-PEG350 (dotted line), DSPE-PEG750 (dashed line), 1-O-DPPE-PEG2000 (solid line) suspended in a 10 mM HEPES-buffer (pH=7.5). Phospholipase A$_2$ (25 nM) was added at time 1200 sec and the temperature was 41° C. The percentage of calcein released is determined as described in FIG. 4. PLA$_2$ catalysed hydrolysis of 1-O-DPPE-PEG350 induced the fastest and highest release.

The concentrations of D-O-SPC and polymer lipid micelles were 25 µM. Snake venom $PLA_2$ (*Agkistrodon piscivorus piscivorus*) was added (25 nM) to initiate the hydrolytic reaction leading to instant formation of the lyso-1-O-PPE and the free fatty acid hydrolysis products. As calcein is released from the D-O-SPC liposomes, due to the incorporation of the non-bilayer forming polymer-lyso-1-O-lipid and fatty acid into the target lipid membrane, a linear increase in the fluorescence at 520 nm after excitation at 492 nm is observed when calcein is diluted into the surrounding buffer medium as shown in FIG. 8. The percentage of calcein released is determined as described in example 3. $PLA_2$ catalysed hydrolysis of 1-O-DPPE-PEG350 induced the fastest release rate, whereas the DPPE with the longest polymer chain (PEG2000) attached to the head group induced the slowest rate of release.

Example 9

Hydrolysis of Micelles Composed of DSPE-PEG750

Figure 9:
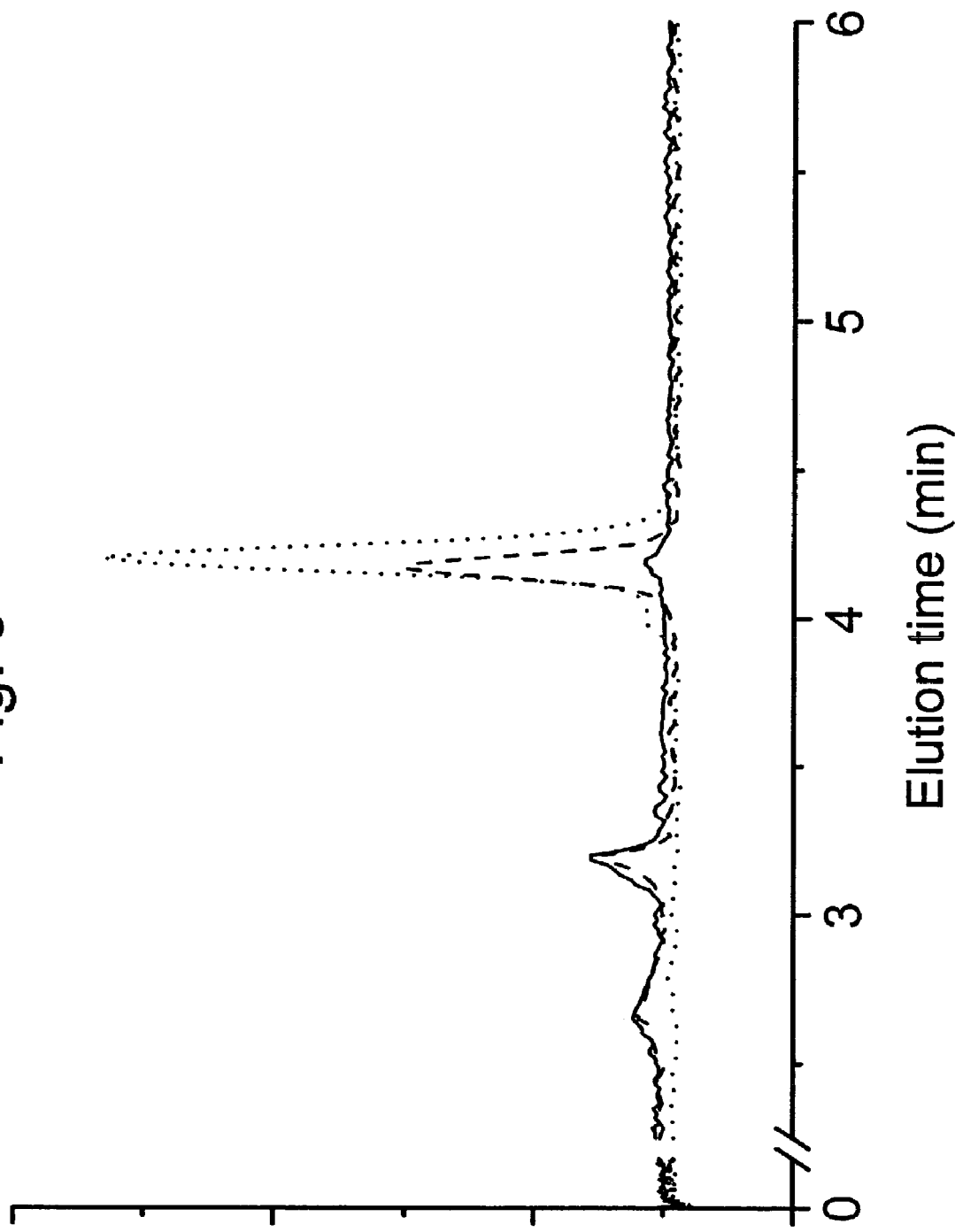
FIG. 9. HPLC chromatograms illustrating the effect of phospholipase A$_2$ hydrolysis of micelles composed DSPE-PEG750 (0.150 mM). The chromatograms show the amount of stearic acid generated before (solid line) phospholipase. A$_2$ (*A. piscivorus piscivorus*) was added to the micelle suspension and the amount (dashed line) of DSPE-PEG750 after the lag-burst. The dotted line show pure stearic acid (0.4 mM). The percentage hydrolysis was calculated on basis of the integrated area of the stearic acid standard (115850 units) and the integrated area of the sample (45630 units). The concentration of the stearic acid in the sample was calculated to (45630/115850×0.4 mM) 0.157 mM, which means that 100% of the DSPE-PEG750 was hydrolysed to lyso-SPE-PEG750 and stearic acid.

The hydrolysis of micelles composed DSPE-PEG750 was followed by analysis of the amount of stearic acid generated. The catalytic reaction was initiated by adding 8.9 µL of a 42 µM $PLA_2$ (150 nM) stock solution to 2.5 ml a thermostated micelle suspension of DSPE-PEG750 (0.150 mM) equilibrated at 45° C. for 600 seconds prior to addition of $PLA_2$. The characteristic burst behaviour of $PLA_2$ towards the micelles is signalled by a sudden increase in the intrinsic fluorescence from $PLA_2$ at 340 nm after excitation at 285 nm followed by a concomitant decrease in the 90° light scattering from the lipid suspension (Hønger et al., *Biochemistry* 35, 9003-9006). Samples for HPLC analysis of the amount of stearic acid generated were taken before adding $PLA_2$ and 100 sec after the observed lag-time. The HPLC chromatograms in FIG. 9 shows the amount of stearic acid generated 100 sec after the observed lag time (10 sec) at 45° C. The amount (0.156 mM) of stearic acid generated by hydrolysis was equal to 100% hydrolysis of the DSPE-PEG750 polymer-lipids. HPLC analysis was made using a 5 µm diol column, a mobile phase composed of chloroform/methanol/water (730:230:30, v/v) and an evaporative light scattering detector (see example 2).

Example 10

Model Examples

Polymer-coated liposomes can act as versatile label delivery systems due to long vascular circulation time and passive targeting by leaky blood vessels in diseased tissue. In the examples herein are described an experimental model system illustrating a new principle for improved and programmable drug and/or contrast agent delivery which takes advantage of an elevated activity of extracelluar phospholipase $A_2$ at the diseased target tissue. The phospholipase $A_2$ hydrolyses a lipid-based proenhancer in the carrier liposome, producing lyso-phospholipid and free fatty acid, which are shown in a synergistic way to lead to enhanced liposome destabilisation and drug release at the same time as the permeability of the target membrane is enhanced. The proposed system can be made thermosensitive and offers a rational way for developing smart liposome-based drug and/contrast agent delivery systems by incorporating into the carrier specific lipid-based proenhancers, prodestabilisers or prodrugs that automatically become activated by phospholipase $A_2$ only at the diseased target sites, such as inflammed, infected, or cancerous tissue.

The drug and/or contrast agent assumes the altered pharmacokinetics of the liposomal carrier and can in principle be targeted to the diseased tissue by using a combination of physico-chemical and pathophysiological factors at the sites of the liposome carrier and the target membrane, respectively. Liposomes incorporated with glycolipids or lipopolymers, such as polyethylene-glycol (PEG)-lipids, known as liposomes, display an improved stability in the vascular system, possibly due to steric protection caused by the polymer coating. The prolonged circulation time of these liposomes combined with increased vascular porosity of diseased tissue, have formed the basis for positive clinical results for specific systems, including anticancer drugs like doxorubicin as well as antibacterial and anti-inflammatory drugs as well as specific contrast agent delivery systems for imaging purposes (e.g. Mn-based MR imaging agents) Niesman et al., J. Liposome Res. 4, 939-957; Koenig and Brown, Invest. Radiol. 20, 297; Basic et al., Magn. Reson. Med. 13, 44-61; Niesmam et al., Invest. Radiol. 25, 545-551.

Liposomes are self-assembled lipid systems and their stability is therefore to a large extent controlled by non-specific physical interactions. Insight into the molecular control of the physical properties of liposomes is therefore important for manipulating and tailoring the liposomal properties in relation to specific drug-delivery purposes. As an example, the thermally induced gel-fluid lipid phase transition has been exploited and optimised design systems for enhanced release of drugs due to hyperthermia. Recently, programmable fusogenic PEG-liposomes containing the anticancer drug mitoxantrone have been constructed using a time-delayed release of bilayer-stabilising lipids of the liposomes which are accumulated at the tumour sites by extravasation. It would be desirable if an intelligent and versatile drug and/or contrast agent delivery system could be designed which has built in a dual virtual trigger mechanism of simultaneous (i) enhanced drug release selectively at the target tissue and (ii) enhanced transport of the drug and/or contrast agent into the diseased cells. This principle is illustrated schematically in FIG. 11.a.

By the examples herein is described the development of a simple and operative experimental biophysical model system which sustains such a dual mechanism to be triggered at the pathological target sites. The model assumes elevated activity of extracellular phospholipase $A_2$ at the diseased sites as is the case in inflammed and cancerous tissue where the level of extracellular $PLA_2$ can be manifold magnified. Upon exposure to extracellular $PLA_2$, the phospholipids of the PEG-liposomes have been shown to suffer enhanced hydrolysis compared to conventional bare liposomes. This leads to destabilisation of the liposome and enhanced release of the encapsulated drug. The hydrolysis products, lyso-phospholipids and free fatty acids, act in turn as absorption enhancers for drug and/or contrast agent permeation across the target membrane. In this way the phospholipids of the carrier liposome behave as prodestabilisers at the site of the carrier and as proenhancers at the site of the target membrane. Molecular details of this principle are illustrated schematically in FIG. 11.b.

The experimental model system consists of bare liposomes, polymer-coated liposome carrier and a model target membrane. The carrier is a 100 nm unilamellar liposome made of dipalmitoyl phosphatidylcholine lipids (DPPC) with 2.5 mol % lipopolymer of the type dipalmitoyl phosphatidylethanolamine (DPPE)-$PEG_{2000}$. The target membrane is another liposome made of 1,2-O-dioctadecyl-sn-glycero-phosphatidylcholine (D-O-SPC) which is a phospholipid where the acyl linkages of the stearoyl chains are ether bonds. In contrast to DPPC, D-O-SPC is inert towards $PLA_2$-catalysed hydrolysis thereby mimicking the stability of an intact target cell membrane toward degradation by its own enzymes. This experimental assay, which permits simultaneous as well as separate investigation of the effect of destabilisers at the carrier liposomes and the effect of enhancers at the target membrane, involves entrapment of a water-soluble fluorescent calcein model drug and/or contrast agent in a self-quenching concentration, in the interior of the non-hydrolysable target liposome, rather than in the carrier liposome. The enhanced level of extracellular $PLA_2$ at the target membrane can then be simulated by adding extracellular $PLA_2$ to initiate the hydrolytic reaction in a suspension of the carrier and target liposomes. The permeation of calcein across the D-O-SPC target membrane is subsequently monitored by the increase in fluorescence. In order to investigate the effect of the presence of the PEG-lipids in the carrier liposome, a similar experiment was performed with conventional bare DPPC liposomes, which advantageously can be used for targeting of macrophage-rich organs of RES such as the liver and spleen. Furthermore, in order to compare and discriminate the permeability enhancing effect of lyso-phospholipids from that of free fatty acids, experiments without enzymes were carried out where lyso-phospholipids and free fatty acids were added simultaneously or separately to the target liposomes.

In FIG. 12.a are shown the results for the release of calcein as a function of time after adding $PLA_2$ to the system. The reaction time-course of the particular $PLA_2$ used has a characteristic lag-burst behaviour with a so-called lag time which conveniently can be used as a measure of the enzymatic activity. A dramatic decrease in the lag time and a concomitant enhancement of the rate of release are observed when the carrier liposomes contain the lipopolymers, DPPE-$PEG_{2000}$, in accordance with previous findings of enhanced extracellular $PLA_2$ degradation of polymer-coated liposomes.

These results suggest that the products of the $PLA_2$-catalysed hydrolysis of the DPPC lipids of the DPPC-lipsomal carrier, lyso-phospholipid and free fatty acid, which are produced in a 1:1 mixture, are incorporated into the target membrane, leading to a large increase in membrane permeability. These products, which have very low water solubility, are known, due to their non-cylindrical molecular shapes, to induce a curvature stress field in the membrane or small-scale lateral phase separation which induce membrane defects and increased permeability. This is substantiated by the data in FIG. 13 which show that the addition of lyso-phospholipid or fatty acid separately to the present target system, in the absence of $PLA_2$, leads to an increased rate of calcein release across the target membrane. However, the crucial finding is that if lyso-phospholipid and free fatty acid are added simultaneously in a 1:1 mixture, a dramatic enhancement in the rate of release is observed as shown in FIG. 13. This strongly suggests that the two enhancers act in a synergistic fashion, thereby highlighting the unique possibility in exploiting $PLA_2$-catalysed hydrolysis for combined destabilisation of the carrier liposome and enhancement of drug transport across the target membrane. The synergistic effect is further augmented by the fact that extracellular $PLA_2$ is activated by its own hydrolysis products revealing the degradable phospholipids of the carrier liposome as a kind of proactivators.

It should be pointed out that the effect in the present drug and/or contrast agent delivery model system of using lipids as proenhancers and prodestabilisers via extracellular $PLA_2$ activity is dynamic and refers to an intrinsic time scale. This time scale is the effective retention time of the carrier liposomes near the target membrane. The more rapidly the enzyme becomes active, the faster is the drug and/or contrast agent release and the larger the drug and/or contrast agent absorption during the time which the carrier spends near the target. Furthermore, the faster the enzyme works the more readily it becomes available for hydrolysis of other drug-carrying liposomes that approach the diseased target site. Once it has been established that extracellular $PLA_2$ activity can be used to control drug release, several rational ways open up for intelligent improvements of the proposed drug and/or contrast agent delivery system via use of well-known mechanisms of altering extracellular $PLA_2$ activity by manipulating the physical properties of the lipid bilayer to which the enzyme is known to be sensitive. Hence the strategy is to modify certain physical properties of the carrier liposomes without significantly changing their vascular circulation time. We shall illustrate this general principle by demonstrating the effects of both a physico-chemical factor, the lipid composition of the carrier, and an enviromental (thermodynamic) factor, the local temperature at the target site.

Short-chain phospholipids, such as didecanoyl phosphatidylcholine (DCPC), activate extracellular $PLA_2$. The effect on calcein permeation across the target membranes induced by incorporation of a small amount of DCPC into the carrier PEG-liposomes is also shown in FIG. 12.a. The release is very fast due to an almost instantaneous activation of the enzyme. We have furthermore found that extracellular $PLA_2$ becomes deactivated (data not shown) when a large amount of cholesterol (≈20 mol %) is incorporated into liposomes. In contrast we find that a small amount of cholesterol (≈3 mol %) activates extracellular $PLA_2$. These significant findings are of particular interest since the blood circulation time of PEG-liposomes has been reported to be almost the same without cholesterol as with large amounts of cholesterol.

Temperature is known to have a dramatic and highly non-linear effect on extracellular $PLA_2$ activation in the region of the gel-fluid phase transition of saturated phospholipid bilayers. This effect is not caused by changes in the enzyme but by dramatic lateral structural changes in the lipid bilayer. It is possible to take advantage of this effect in the present drug and/or contrast agent delivery system as suggested by the data in FIG. 12.b. As the temperature approaches the transition temperature at 41° C., the rate of calcein release is progressively enhanced as quantified by the time of 50% calcein release, $t_{50\%}$, shown in the insert to FIG. 12.b. It has previously been suggested that hypertermia could be exploited to enhance drug release, and that local heating at predefined tumour areas could be used to locally destabilise drug-carrying liposomes, by exploiting the enhanced leakiness of liposomes at their phase transition. In the new model drug and/or contrast agent delivery system proposed here, these thermosensitive possibilities are integrated and fully exploited via the thermal sensitivity of extracellular $PLA_2$ to the physical properties of the carrier liposome. In contrast to the case where the thermic effect can only be achieved by a local temperature increase using external heating sources at a predetermined tumour site of some minimal size, the $PLA_2$-controlled release will be enhanced everywhere where temperature and extracellular $PLA_2$ concentration are elevated, e.g. in inflammed tissue, independent of the size of the diseased region and without requiring a preceding localisation of the diseased tissue.

DPPC, DCPC, D-O-SPC, and DPPE-$PEG_{2000}$ were obtained from Avanti Polar Lipids. The DPPE-$PEG_{2000}$ lipopolymer contains 45 monomers in the PEG polymer chain. Purified snake venom $PLA_2$ (*Agkistrodon piscivorus piscivorus*) was a generous gift from dr. R. L. Biltonen. This $PLA_2$ enzyme belongs to the class of low-molecular weight, 14 kD secretory enzymes which display structural similarity to human extracellular phospholipase $A_2$. Multilamellar target liposomes in the presence of fluorescent calcein in a self-quenching concentration of 20 mM were made by hydrating a film of D-O-SPC in a HEPES buffer solution at pH=7.5 for one hour at 10° C. above the phase transition temperature $T_m$=55° C. Unilamellar liposomes were made by extruding the multilamellar liposomes ten times through two stacked 100 nm polycarbonate filters. The unilamellar liposomes were rapidly cooled to a temperature below the transition temperature, and the calcein-containing liposomes were separated from free calcein using a chromatographic column packed with Sephadex G-50. The unilamellar carrier liposomes of DPPC, DCPC and DPPE-$PEG_{2000}$ were prepared in a similar fashion $T_m$=41° C.). Calcein release from the target liposomes is determined by measuring the fluorescent intensity at 520 nm after excitation at 492 nm. All measurements are performed at temperatures where the lipids of both the carrier and target liposomes are in the gel state.

Example 11

Phospholipase $A_2$ Concentration Dependent Release Assay

Multilamellar 1-O-DPPC-liposomes with 10 mol % 1-O-DPPE-PEG350 were made in the presence of fluorescent calcein in a self-quenching concentration of 20 mM by hydrating a film of 90% 1-O-hexadecyl-2-hexadecanoyl-sn-glycero-3-phosphocholine and 10% 1-O-hexadecyl-2-hexadecanoyl-sn-glycero-3-phosphoethanolamine-N-[methoxy (polyethylene glycol)-350] in a HEPES buffer solution at pH=7.5 for one hour at 10° C. above the phase transition temperature. Unilamellar liposomes were formed by extruding the multilamellar liposomes ten times through two stacked 100 nm polycarbonate filters. The unilamellar liposomes were rapidly cooled to a temperature below the transition temperature, and the calcein-containing liposomes were separated from free calcein using a chromatographic column packed with Sephadex G-50.

Assay conditions for the $PLA_2$ induced calcein release were 25 μM unilamellar liposomes, 50, 1 and 0.02 nM $PLA_2$,150 mM KCL, 10 mM HEPES (pH 7.5), 1 mM $NaN_3$, 30 μM $CaCl_2$, and 10 μM EDTA. $PLA_2$ was added to 2.5 ml of the thermostated lipid suspension equilibrated for at least 300 sec at 35.5° C. prior to addition of $PLA_2$. The percentage of calcein released is determined as: % Release=$100 \times (I_{F(t)} - I_B)/(I_T - I_B)$, where $I_{F(t)}$ is the measured fluorescence at time t after addition of the enzyme, $I_B$ is the background fluorescence, and $I_T$ is the total fluorescence measured after addition of Triton X-100 which leads to complete release of calcein by breaking up the 1-O-DPPC-liposomes. FIG. 14 show that the induced release of calcein was slowest when only 0.02 nM $PLA_2$ was added to the liposome suspension.

Example 12

In vivo Hemolysis

Assay

Groups of mice (n=5/group; weight 18-22 g) were treated i.v. with buffer (PBS), ET-18-$OCH_3$ (50 mg/kg), and liposomes composed of 1-O-DPPC with 5 mol % 1-O-DPPE-PEG2000 (68.7 and 137.5 mg/kg). 30 min after injection, 100 μl blood was collected into heparinised tubes directly from decapitated, $CO_2$-anesthetised mice. The blood was centrifuged at 500×G for 10 min, and plasma was removed and stored at −20° C. until analysed.

The degree of hemolysis was measured by absorbance at 550 nm using a Perkin-Elmer 320 scanning spectrophotometer. 25 μl plasma was mixed with 2,5 ml PBS or 2.5 ml 10% triton X-100. 100 percent hemolysis was defined as the maximum amount of hemolysis obtained from the plasma of PBS treated mice mixed with 10% Triton X-100 and 0 percent as plasma from PBS treated mice mixed with PBS.

The hemolysis profile in table 2 shows a low hemolysis value for the mice treated with 2 mM liposomes composed of 1-O-DPPC with 5 mol % 1-O-DPPE-PEG2000. The mice treated with ET-18-$OCH_3$ died within the 30 minutes period.

TABLE 2

Percent hemolysis, ± standard error, after 30 min and the number of surviving mice in each group.

| Treatment | PBS | ET-18-OCH$_3$ 50 mg/kg | 1-O-DPPC with 5 mol % 68.7 mg/kg | 1-O-DPPE-PEG2000 137.5 mg/kg |
|---|---|---|---|---|
| Hemolysis | 1.7% (± 0.2) | ND (died) | 4.0% (± 2.4) | 6.6% (± 0.7) |
| Survival (30 min) | 3/3 | 0/5 | 5/5 | 5/5 |

As used herein, "solid tumours" are those growing in an anatomical site other than the bloodstream (in contrast to blood-borne tumours such as leukemias). Solid tumours require the formation of small blood vessels and capillaries to nourish the growing tumour tissue.

Example 13

Hydrolysis of Negatively Charged Liposomes by Phospholipase A2 in Cell-Free Rat Peritoneal Fluid Cell-free peritoneal fluid from rat with casein-induced acute inflammation was prepared by injecting 5 ml 1% sodium caseinate into the peritoneal cavity of a SRPD male rat, weighing 250-260 g. The rat was sacrificed by bleeding after 24 hours and the inflammatory fluid was collected from the peritoneum and centrifuged at 1500 G for 20 min in order to obtain a cell-free peritoneal fluid.

Negatively charged fully hydrated unilamellar liposomes with a narrow size distribution were prepared from 89 mol % di-hexadecanoyl-sn-glycero-3-phosphoglycerol (DPPG), 10 mol % 1-O-hexadecyl-2-hexadecanoyl-sn-glycero-3-phosphoethanolamine-N-[methoxy(polyethylene glycol)-350] (1-O-DPPE-PEG350) and 1 mol % 1,2-bis-(1-pyrenedecanoyl)-sn-glycero-3-phosphocholine (bis-py-DPC). Bis-py-DPC is a PLA2 substrate with two adjacent pyrene fluorophores that form excited-state dimers (eximers) emitting at 470 nm upon excitation at 342 nm. Phospholipase catalysed hydrolysis separates the two fluorophores, which then emit at 380 nm (monomers).

FIG. 15 shows the emission spectra obtained after excitation at 342 nm of bis-py-DPC incorporated in negatively charged liposomes (0.100 mM) before and after adding 100 nM PLA$_2$ (*Agkistrodon piscivorus piscivorus*). The observed change in the emission spectrum after phospholipase mediated hydrolysis is used in a continues assay, measuring the eximer emission at 470 nm simultaneously with the monomer emission at 380, upon excitation at 342 nm. FIG. 16 shows the reaction time profile of rat phospholipase A$_2$ catalysed hydrolysis of the negatively charged liposomes. The catalytic reaction was initiated by adding cell-free peritoneal fluid to 2.5 ml of a thermostated liposome suspension equilibrated for 60 sec prior to addition of PLA$_2$. The characteristic lag-burst behaviour of the phospholipase is signalled by a sudden increase in the monomer fluorescence at 380 nm and a subsequent decrease in the eximer fluorescence as shown at the insert on FIG. 16.

Assay conditions for the PLA$_2$ reaction time profile shown in FIG. 16 were: 0.100 mM unilamellar negatively charged liposomes, 100 µl undiluted cell-free peritoneal fluid, 10 mM HEPES (pH 7.5), 5 mM CaCl$_2$, and 150 mM NaCl.

References

Torchilin, V. P. (1998) Liposomes as carriers of contrast agents for in vivo diagnostics. In: Lasic and Papahadjopoulos (eds.) Medical Applications of Liposomes. Elsevier Science p. 515-543.

Kaiser, E. (1999) Phospholipase A2: its usefulness in laboratory diagnostics.Crit Rev Clin Lab Sci 36(2):65-163

The invention claimed is:

1. A method for identifying malignant tissue in a mammal, wherein said malignant tissue is a member selected from the group consisting of lung cancer, ovarian cancer and sarcoma tissue, said method comprising:
   a) administering a lipid-based system comprising a lipid derivative and a label to an individual suspected of having a malignant disease characterised by having an elevated PLA$_2$ level whereby said label is released from said lipid derivative to the malignant tissue, and
   b) detecting said label, thereby identifying said malignant tissue, and wherein said lipid derivative constitutes 50-100 mol % of said lipid-based system, and wherein said lipid derivative has the following formula:

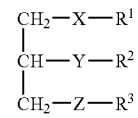

wherein
   X and Z are O;
   Y is —OC(O)—, Y then being connected to R$^2$ via either the oxygen or carbonyl carbon atom;
   R$^1$ is an aliphatic group of the formula Y$^1$Y$^2$;
   R$^2$ is an organic radical having at least 7 carbon atoms;
   where Y$^1$ is —(CH$_2$)$_{n1}$—(CH=CH)$_{n2}$—(CH$_2$)$_{n3}$—(CH=CH)$_{n4}$—(CH$_2$)$_{n5}$—(CH=CH)$_{n6}$—(CH$_2$)$_{n7}$—(CH=CH)$_{n8}$—(CH$_2$)$_{n9}$, and the sum n1+2n2+n3+2n4+n5+2n6+n7+2n8+n9 is an integer of from 9 to 29; n1 is zero or an integer of from 1 to 29, n3 is zero or an integer of from 1 to 20, n5 is zero or an integer of from 1 to 17, n7 is zero or an integer of from 1 to 14, and n9 is zero or an integer of from 1 to 11; and each of n2, n4, n6 and n8 is independently zero or 1; and Y$^2$ is CH$_3$ or CO$_2$H; where each Y$^1$—Y$^2$ independently may be substituted with halogen or C14-alkyl, and
   R$^3$ is selected from phosphatidic acid (PO$_2$-OH), derivatives of phosphatidic acid and bioisosters to phosphatic acid and derivatives thereof.

2. A method according to claim 1, wherein the label is selected from the group consisting of $^{111}$In, $^{99m}$Tc $^{67}$Ga, $^{11}$C, Gd, Mn, iron oxide, argon, nitrogen, Iodine, bromine and barium.

3. A method according to claim 1, wherein R$^2$ is an aliphatic group of a length of at least 7 carbon atoms.

4. A method according to claim 3, wherein $R^2$ is a group of the formula $Y^1Y^2$.

5. A method according to claim 1, wherein the lipid-based system is in the form of liposomes wherein a drug is incorporated.

6. A method according to claim 1, wherein the label is covalently linked to the lipid derivative.

7. A method according to claim 1, wherein the malignant tissue is the primary tumour.

8. A method according to claim 1, wherein the malignant tissue is metastatic cells originating from the primary tumour.

9. A method according to claim 1, wherein the label is detected by a method selected from the group consisting of positron emission tomography (PET), X-ray, gamma-scintigraphy, magnetic resonance (MR) imaging, computed tomography (CT) imaging and ultrasonography.

10. The method according to claim 1, wherein:
$R^1$ and $R^2$ are independently an aliphatic group of the formula $(CH_2)_nCH_3$ wherein n is an integer from 11-29.

11. The method according to claim 10, wherein n is an integer of from 14-16.

12. The method according to claim 4, wherein $R^3$ is a member selected from the group consisting of phosphatidic acid, phosphatidylcholine, phosphatidyl ethanolamine, phosphatidyl serine; phosphatidyl inositol and phosphatidyl glycerol.

13. The method according to claim 10, wherein $R^3$ is a member selected from the group consisting of phosphatidic acid, phosphatidylcholine, phosphatidyl ethanolamine, phosphatidyl serine, phosphatidyl inositol and phosphatidyl glycerol.

14. The method according to claim 11, wherein $R^3$ is a member selected from the group consisting of phosphatidic acid, phosphatidylcholine, phosphatidyl ethanolamine, phosphatidyl serine, phosphatidyl inositol and phosphatidyl glycerol.

15. The method according to any one of claims 10-14, wherein the label is covalently linked to the lipid derivative.

16. The method according to claim 1, wherein said label is quantitatively detected and the amount of said malignant tissue in said mammal is quantified.

17. The method according to claim 16, wherein the label is quantified by a method selected from the group consisting of positron emission tomography (PET), X-ray, gamma-scintigraphy, magnetic resonance (MR) imaging, computed tomography (CT) imaging and ultrasonography.

* * * * *